United States Patent
Guyuron et al.

(10) Patent No.: US 9,283,109 B2
(45) Date of Patent: Mar. 15, 2016

(54) FLUID MANIPULATING DEVICE AND TISSUE INTERACTING DEVICE FOR A THERMAL THERAPY SYSTEM

(75) Inventors: Bahman Guyuron, Lyndhurst, OH (US); Jamie Horvath, Lakewood, OH (US); Paul Tamulewicz, Cleveland, OH (US)

(73) Assignee: Innovative Medical Equipment, LLC, Lyndhurst, OH (US)

( * ) Notice: Subject to any disclaimer, the term of this patent is extended or adjusted under 35 U.S.C. 154(b) by 994 days.

(21) Appl. No.: 12/049,574

(22) Filed: Mar. 17, 2008

(65) Prior Publication Data

US 2008/0228248 A1 Sep. 18, 2008

Related U.S. Application Data

(60) Provisional application No. 60/895,174, filed on Mar. 16, 2007.

(51) Int. Cl.
| | |
|---|---|
| A61F 7/08 | (2006.01) |
| A61F 7/02 | (2006.01) |
| A61F 7/00 | (2006.01) |

(52) U.S. Cl.
CPC .............. *A61F 7/02* (2013.01); *A61F 7/0085* (2013.01); *A61F 2007/0002* (2013.01); *A61F 2007/0004* (2013.01); *A61F 2007/0007* (2013.01); *A61F 2007/0054* (2013.01)

(58) Field of Classification Search
CPC . A61F 7/02; A61F 7/0085; A61F 2007/0054; A61F 2007/0004; A61F 2007/0002; A61F 2007/0007

USPC .................................................. 607/104, 108
See application file for complete search history.

(56) References Cited

U.S. PATENT DOCUMENTS

| | | | |
|---|---|---|---|
| 3,738,367 A | 6/1973 | Hardy | |
| 3,967,627 A | 7/1976 | Brown | |
| 4,108,146 A * | 8/1978 | Golden | 607/104 |
| 4,691,762 A * | 9/1987 | Elkins et al. | 165/46 |
| 4,738,119 A | 4/1988 | Zafred | |
| 4,846,176 A | 7/1989 | Golden | |
| 4,962,761 A | 10/1990 | Golden | |
| 4,998,415 A | 3/1991 | Larsen | |
| 5,097,828 A | 3/1992 | Deutsch | |
| 5,097,829 A * | 3/1992 | Quisenberry | 607/105 |
| 5,320,164 A | 6/1994 | Szczesuil et al. | |
| 5,562,604 A | 10/1996 | Yablon et al. | |
| 5,683,439 A * | 11/1997 | Jensen | 607/104 |
| 5,755,275 A | 5/1998 | Rose et al. | |
| 5,871,526 A * | 2/1999 | Gibbs et al. | 607/104 |
| 5,895,418 A | 4/1999 | Saringer | |
| 6,023,932 A | 2/2000 | Johnston | |
| 6,109,338 A | 8/2000 | Butzer | |
| 6,461,379 B1 * | 10/2002 | Carson et al. | 607/104 |
| 6,502,405 B1 * | 1/2003 | Van Winkle | 62/3.61 |
| 6,508,831 B1 | 1/2003 | Kushnir | |

(Continued)

*Primary Examiner* — Joseph Stoklosa
*Assistant Examiner* — Thomas Giuliani
(74) *Attorney, Agent, or Firm* — Renner, Otto, Boisselle & Sklar, LLP

(57) ABSTRACT

A thermal therapy device (100) comprises a tissue-interacting device (400) which is designed to target one or more significant areas of the therapy-receiving person's body by concentrating the passage of the therapy-providing fluid in these areas. The thermal therapy device (400) can comprise a head pad, eye pads, a knee pad, an ankle/foot pad, an elbow pad, or a neck/shoulder pad.

18 Claims, 37 Drawing Sheets

(56) References Cited

U.S. PATENT DOCUMENTS

| | | |
|---|---|---|
| 6,669,715 B2 * | 12/2003 | Hoglund et al. .............. 607/104 |
| 6,679,908 B2 | 1/2004 | Shimizu |
| 6,770,085 B1 * | 8/2004 | Munson ........................ 607/104 |
| 6,901,608 B2 | 6/2005 | Szczesuil et al. |
| 7,231,777 B1 | 6/2007 | Arnold et al. |
| 7,373,969 B2 | 5/2008 | Chambers |
| 2003/0126866 A1 * | 7/2003 | Spry ................................ 62/3.7 |
| 2004/0249427 A1 | 12/2004 | Nabilsi |
| 2005/0131504 A1 * | 6/2005 | Kim .............................. 607/104 |
| 2005/0187502 A1 * | 8/2005 | Krempel et al. ................... 602/5 |
| 2007/0203552 A1 * | 8/2007 | Machold et al. .............. 607/104 |
| 2008/0188915 A1 | 8/2008 | Mills et al. |

* cited by examiner

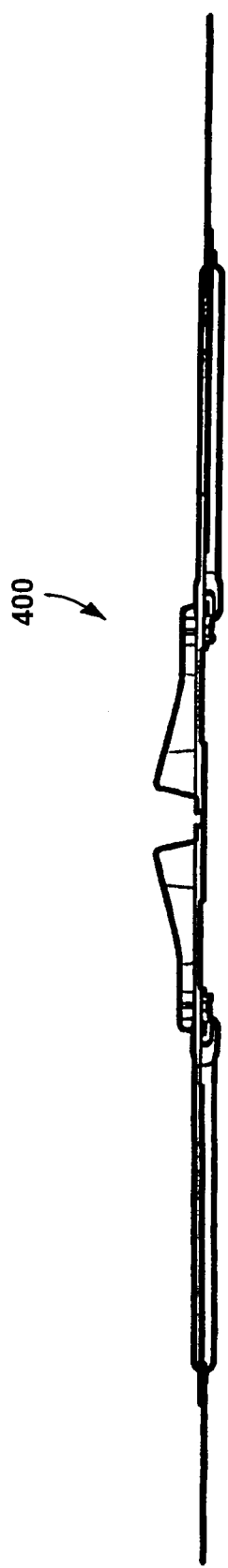

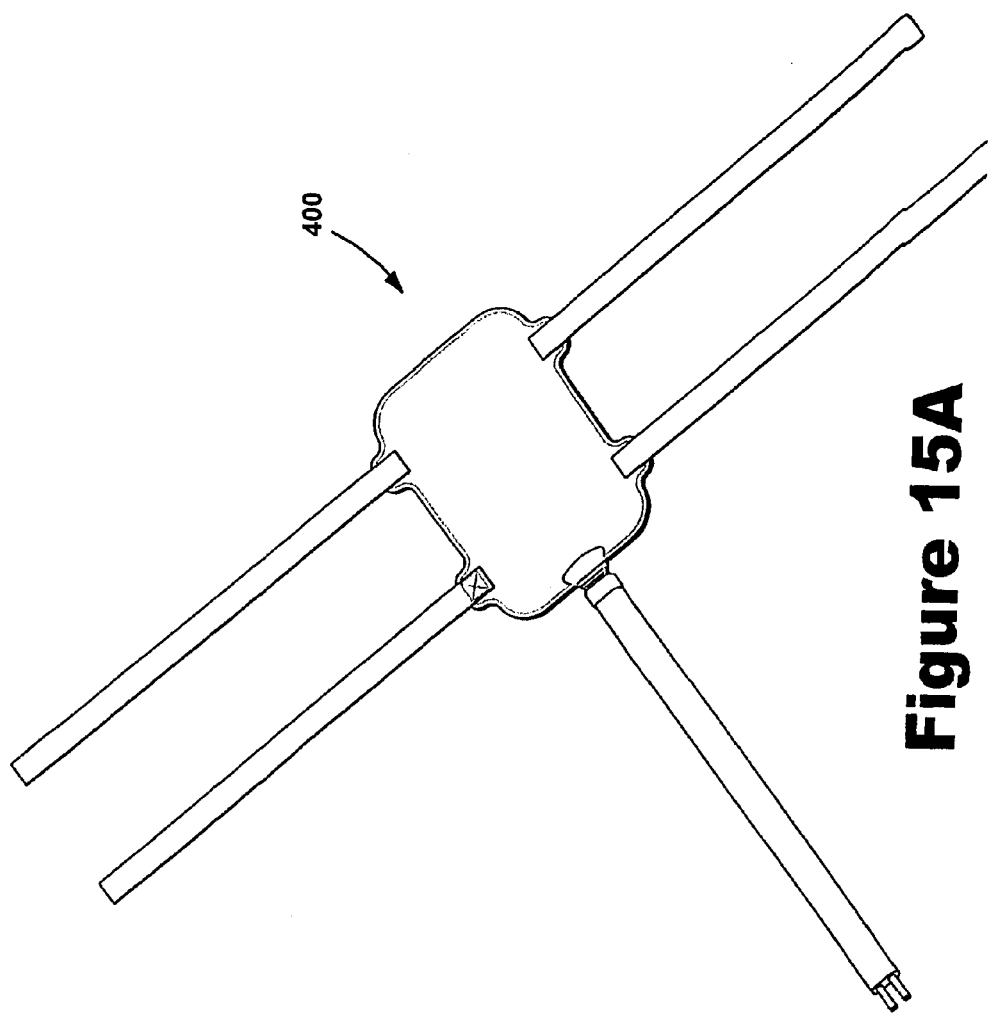

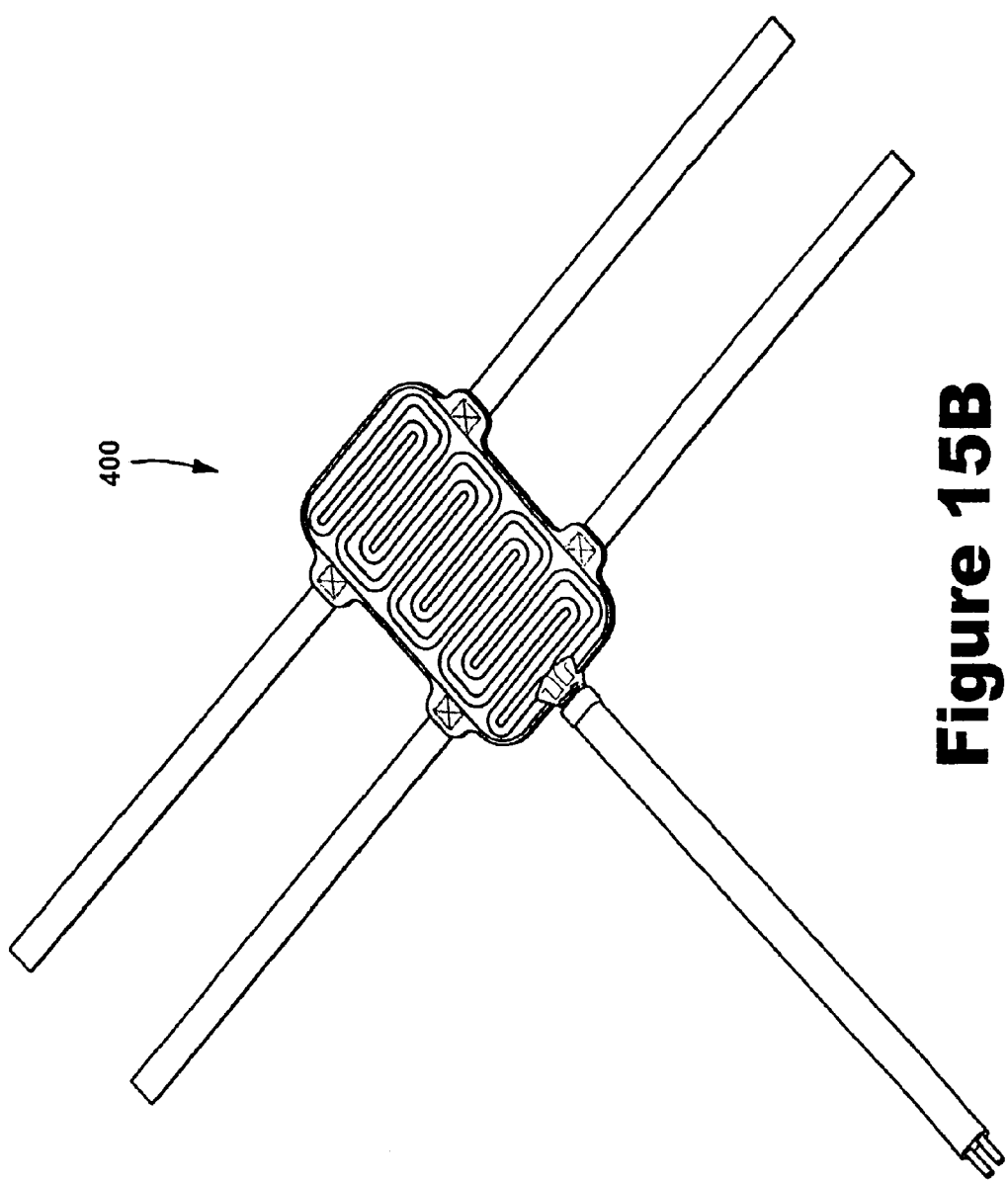

FLUID MANIPULATING DEVICE AND TISSUE INTERACTING DEVICE FOR A THERMAL THERAPY SYSTEM

RELATED APPLICATION

This application claims priority under 35 U.S.C. §119(3) to U.S. Provisional Patent Application No. 60/895,174 filed Mar. 16, 2007. The entire disclosure of this provisional application is hereby incorporated by reference.

GENERAL FIELD

This disclosure relates generally to a thermal therapy system comprising a fluid-manipulating device, which heats/cools and circulates a therapy-providing fluid, and a tissue-interacting device, which contacts tissue on the therapy-receiving person's body.

BACKGROUND

Thermal therapy is the practice of applying heat and/or cold to tissue to reduce swelling/inflamation, to decrease pain, promote healing, increase blood flow, alleviate aches, calm stress points, and/or just for general relaxation. The thermal effect (i.e., heat or cold) can be accomplished by the heating or cooling effect of a therapy-providing fluid (e.g., water, oil) in thermal contact with the relevant tissue. To this end, a tissue-interacting device (containing the therapy-providing fluid) can be strapped or otherwise held in contact with the relevant areas of the therapy-receiving person's body.

DRAWINGS

Figure 5A:
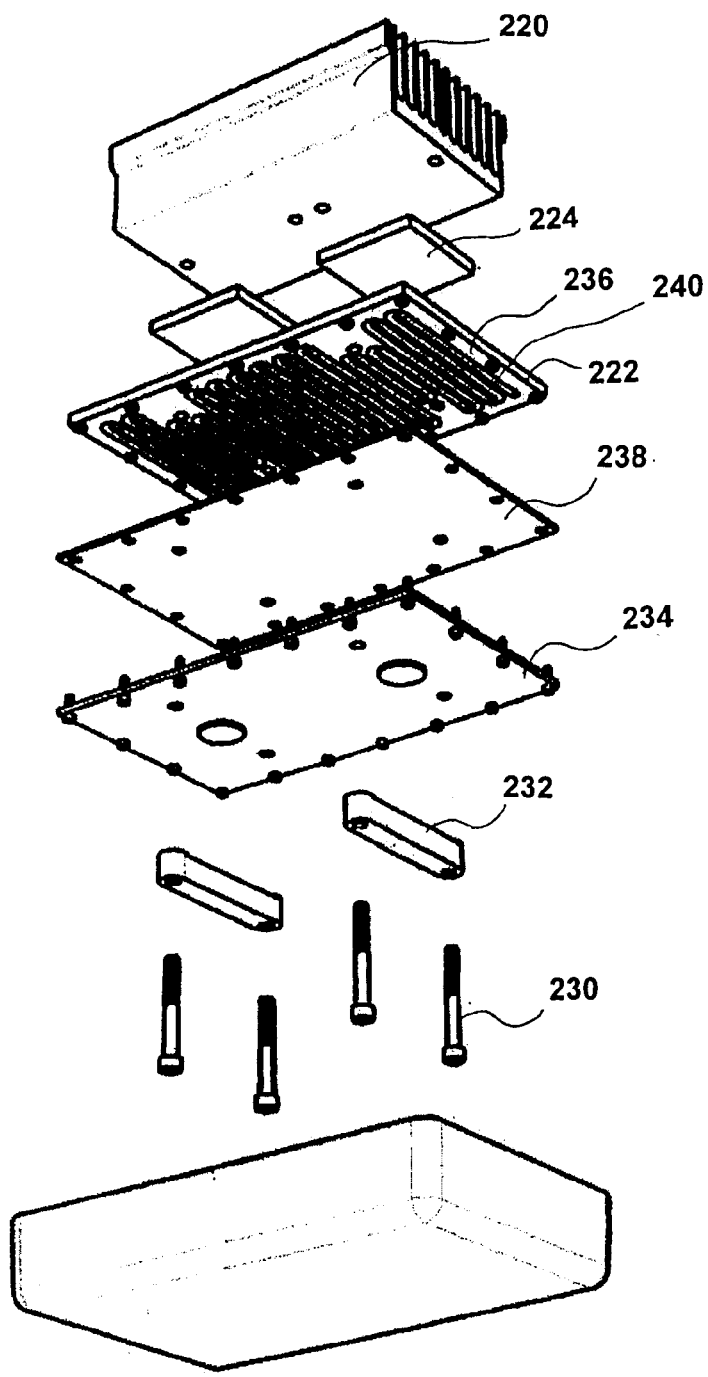
Figure 5B:
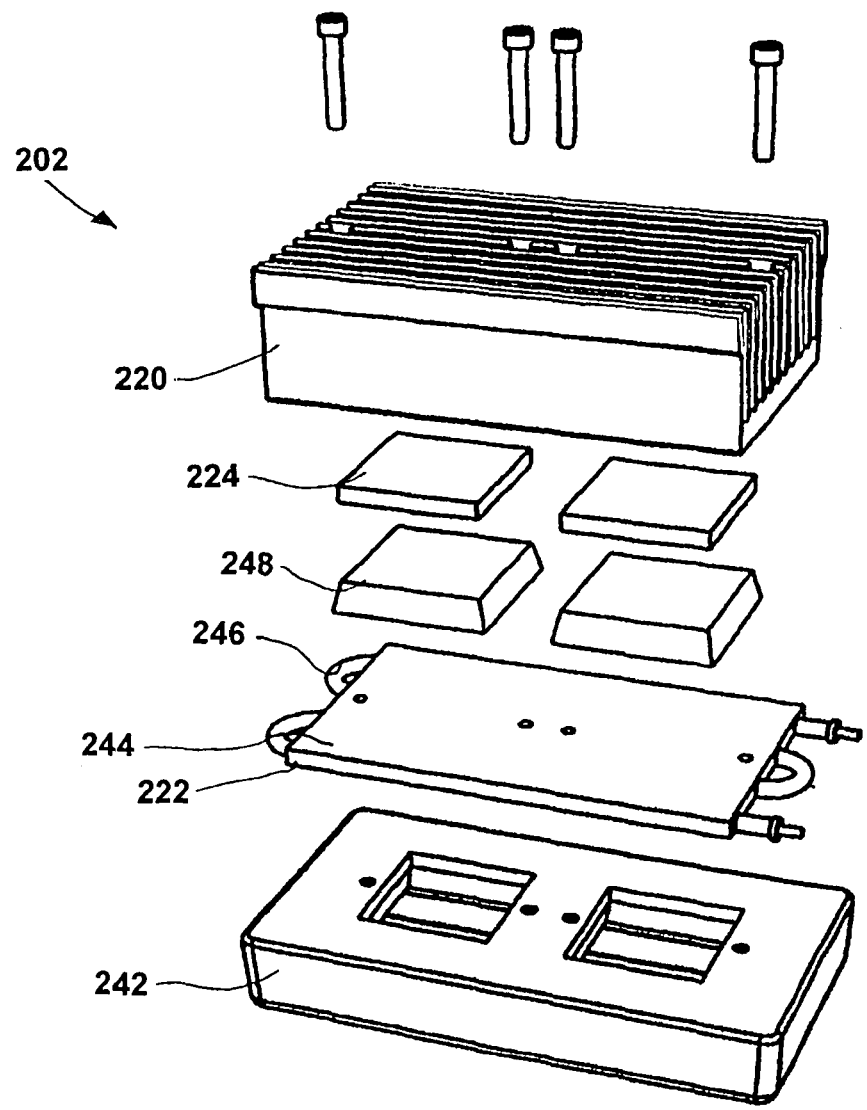
Figure 5C:
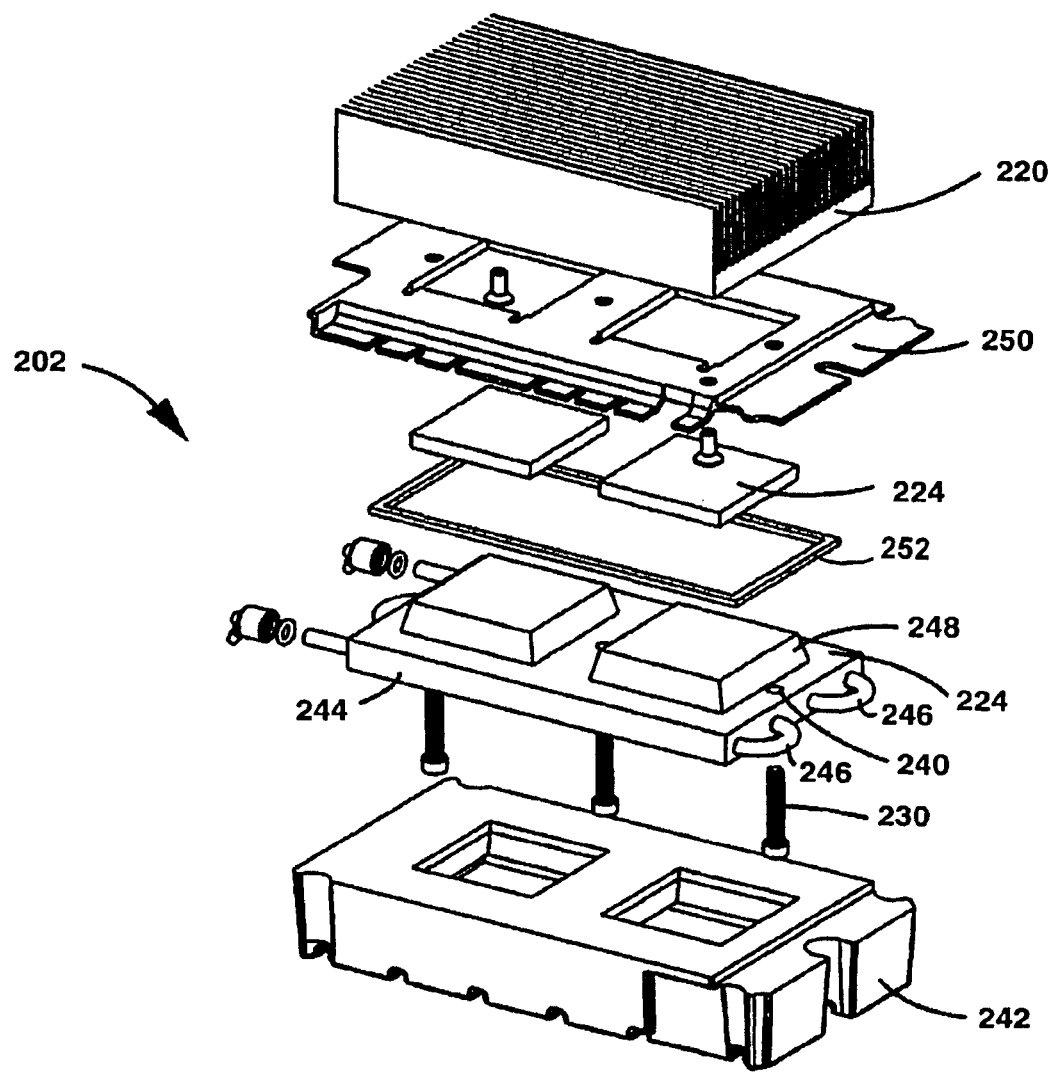

FIGS. 5A, 5B, and 5C are each an exploded view of a heat exchanger.

Figures 6A, 6B:
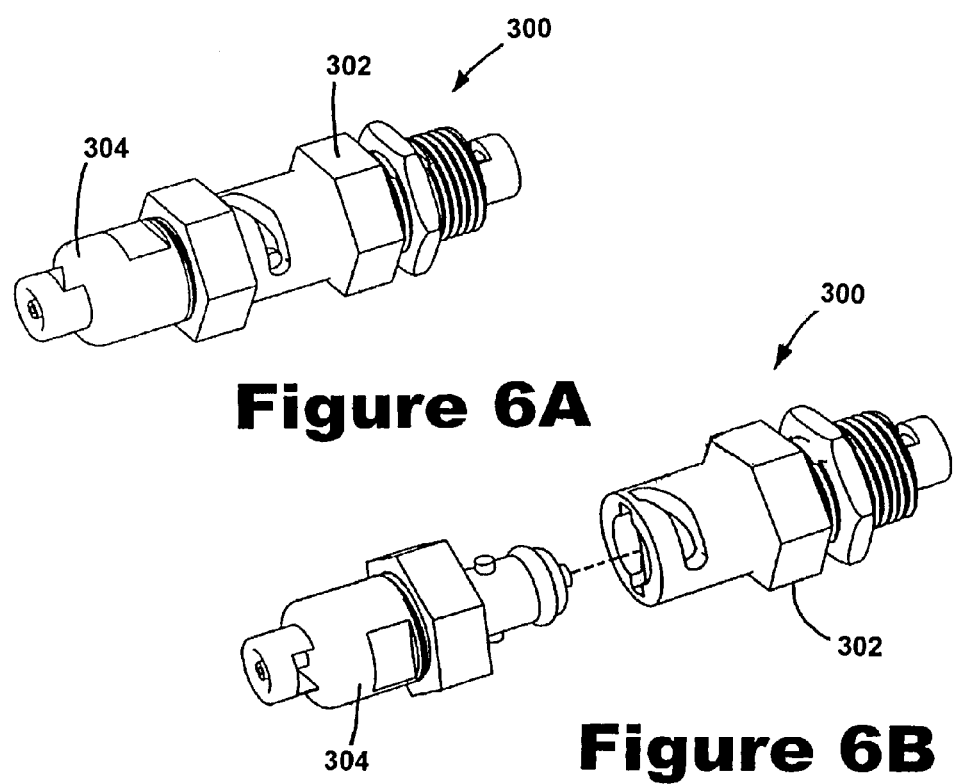

FIGS. 6A and 6B are top perspective views of the preferred coupling that connects the tissue-interacting devices to the fluid-manipulating device, showing the body and insert components of the coupling connected and disconnected, respectively.

Figure 7:
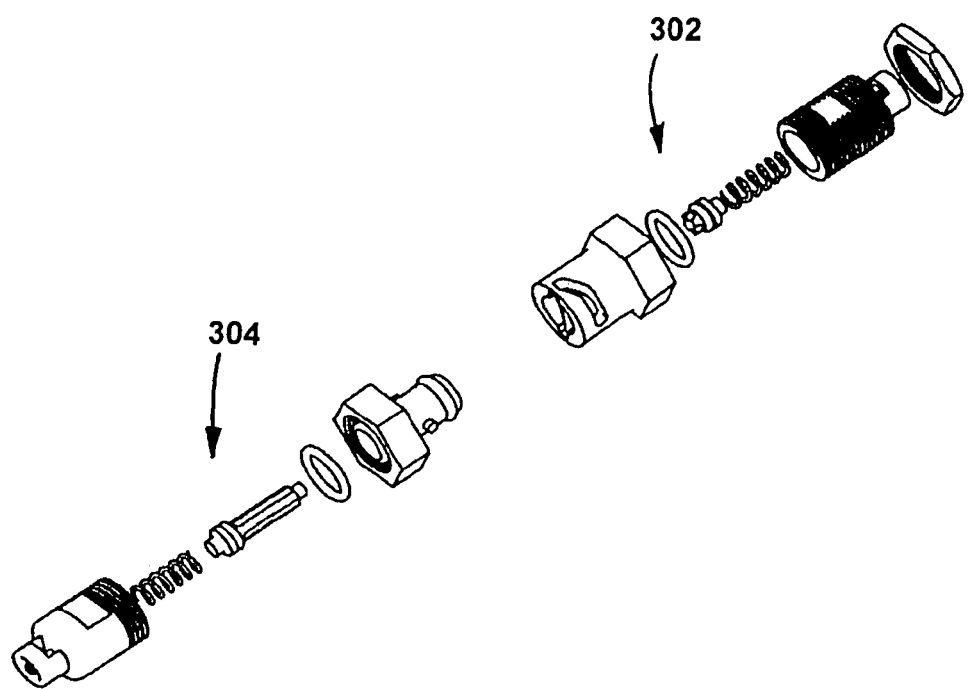

FIG. 7 is an exploded view of the preferred coupling showing the internal valve components.

Figure 8A:
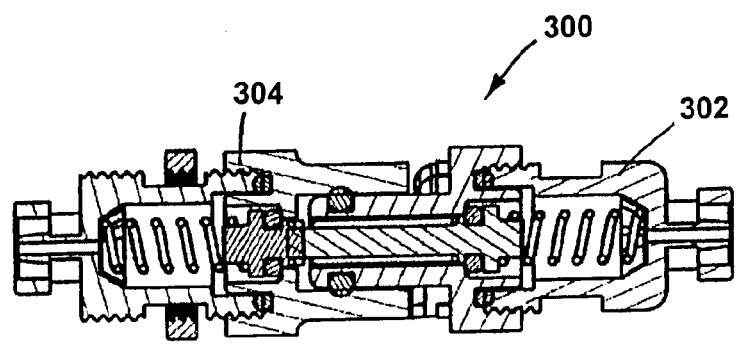
Figure 8:
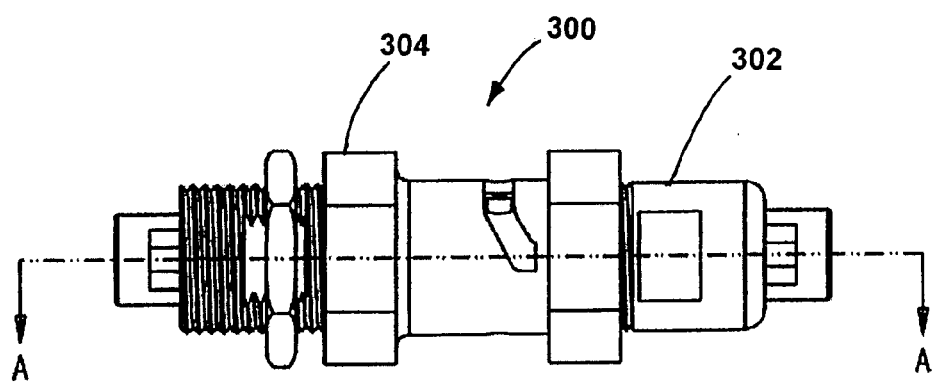

FIG. 8 is a perspective view of a coupling assembly, and FIG. 8A is a cross sectional view of this coupling.

Figure 9A:
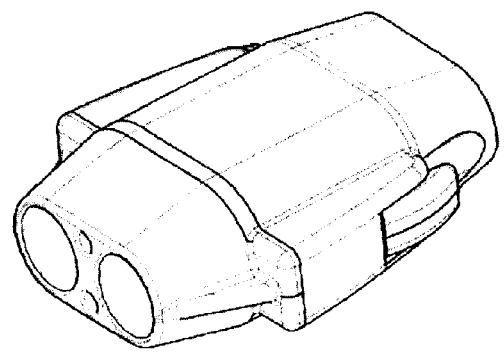
Figure 9B:
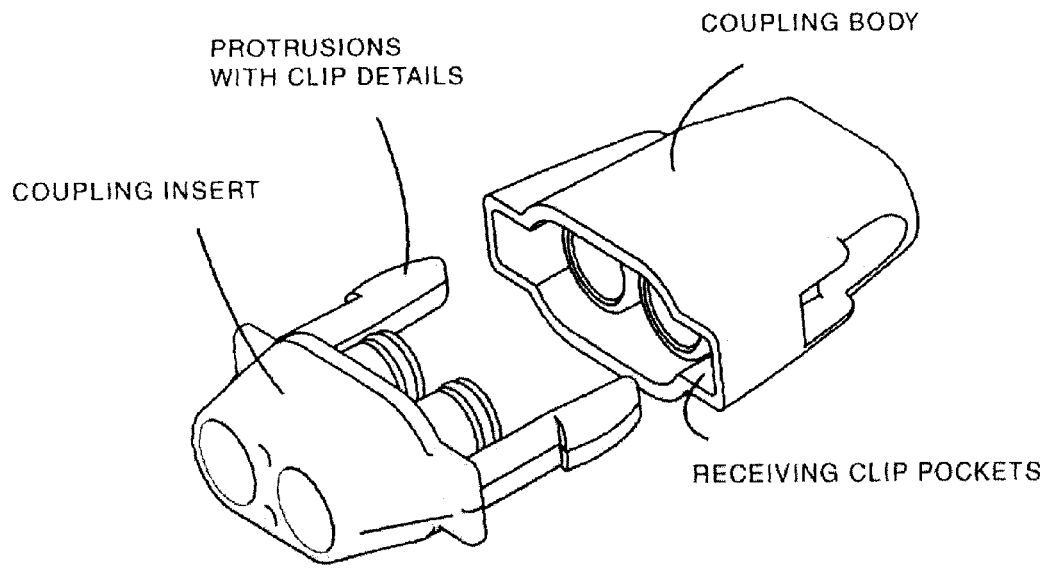

FIGS. 9A and 9B are top perspective views of another coupling assembly.

Figure 10:
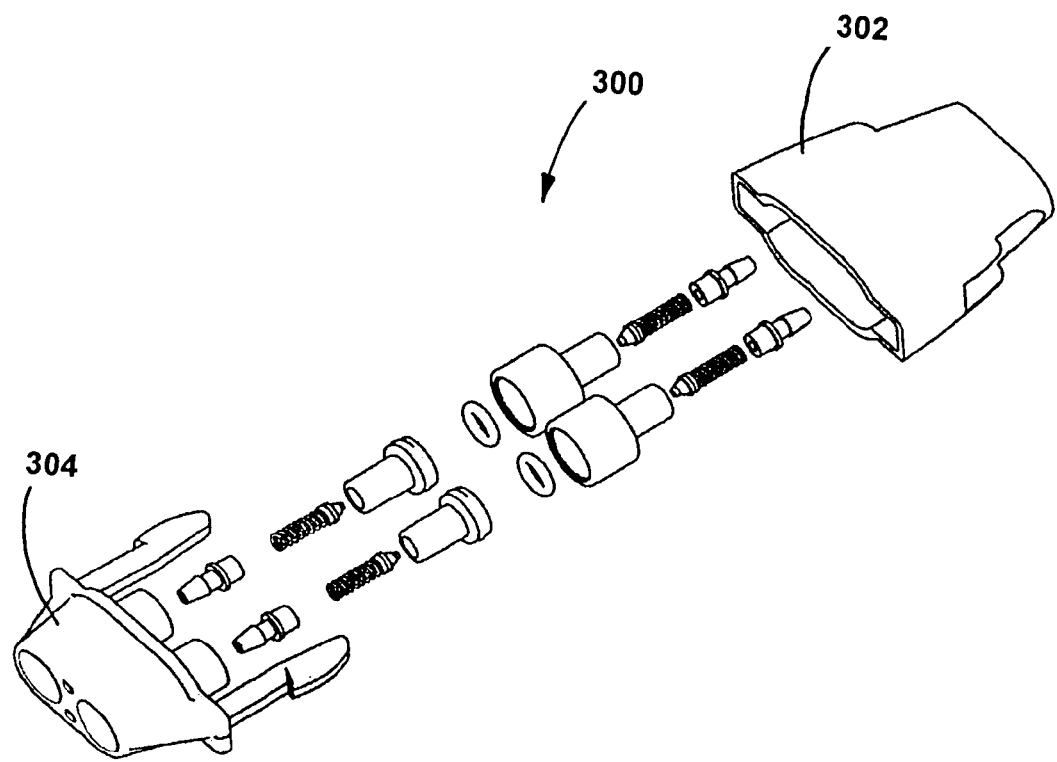

FIG. 10 is an exploded view of another coupling assembly.

Figure 11A:
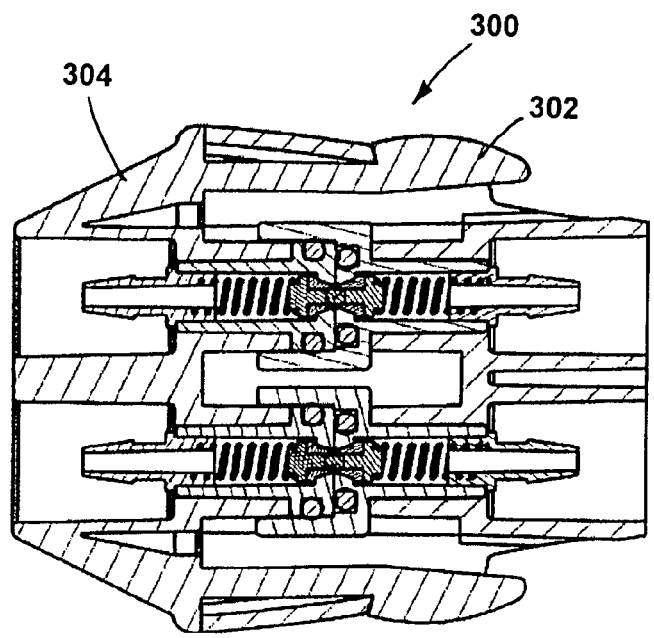
Figure 11:
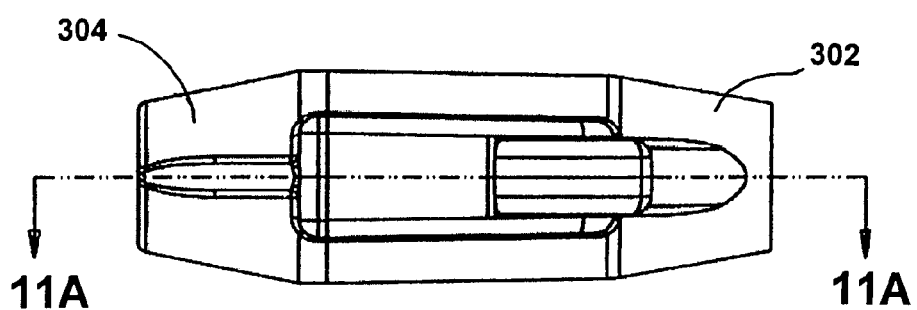

FIG. 11 is a perspective view of another coupling assembly, and FIG. 9A is a cross sectional view of this coupling.

Figure 12A:
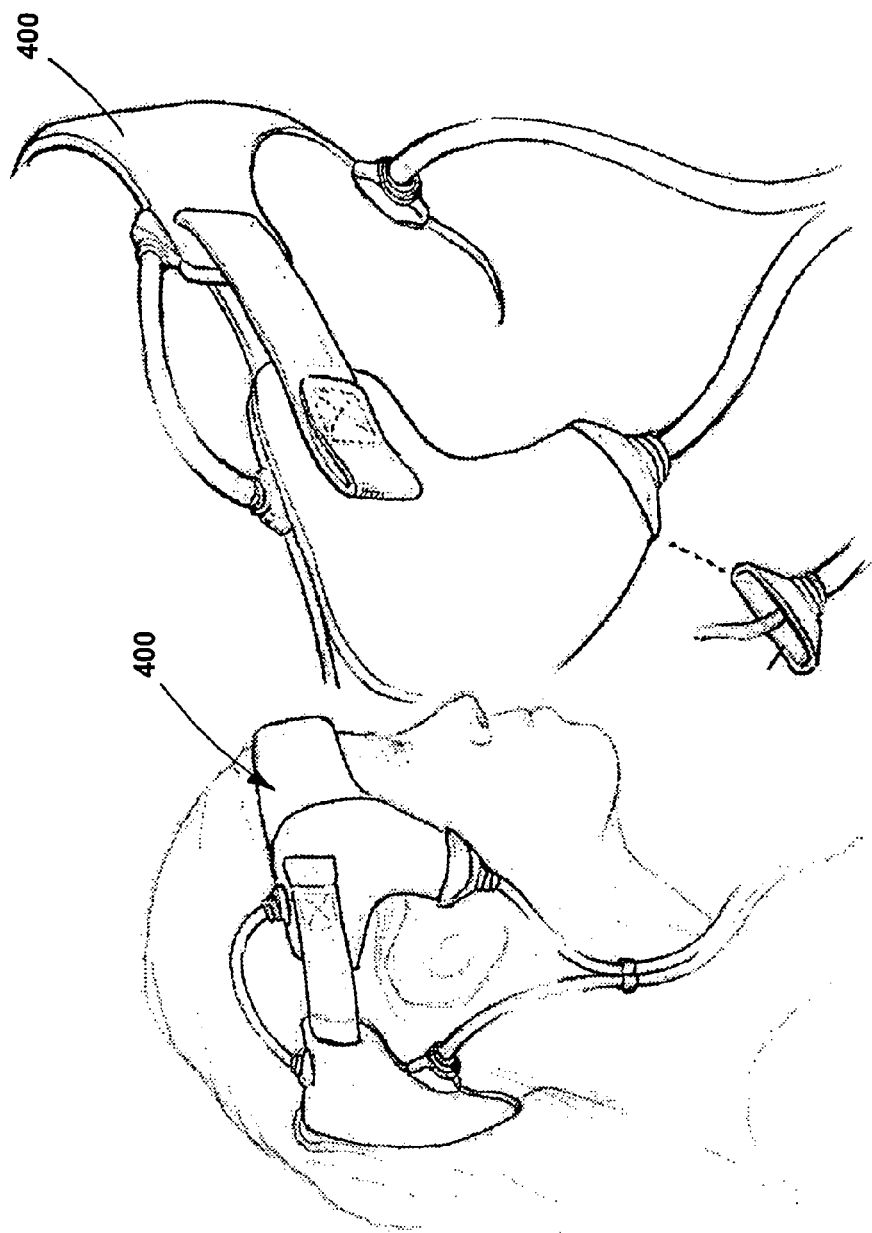

FIG. 12A is a perspective view of the tissue-interacting device in use on the therapy-receiving wearer, this device being a head pad used for migraine treatment.

Figure 12B:
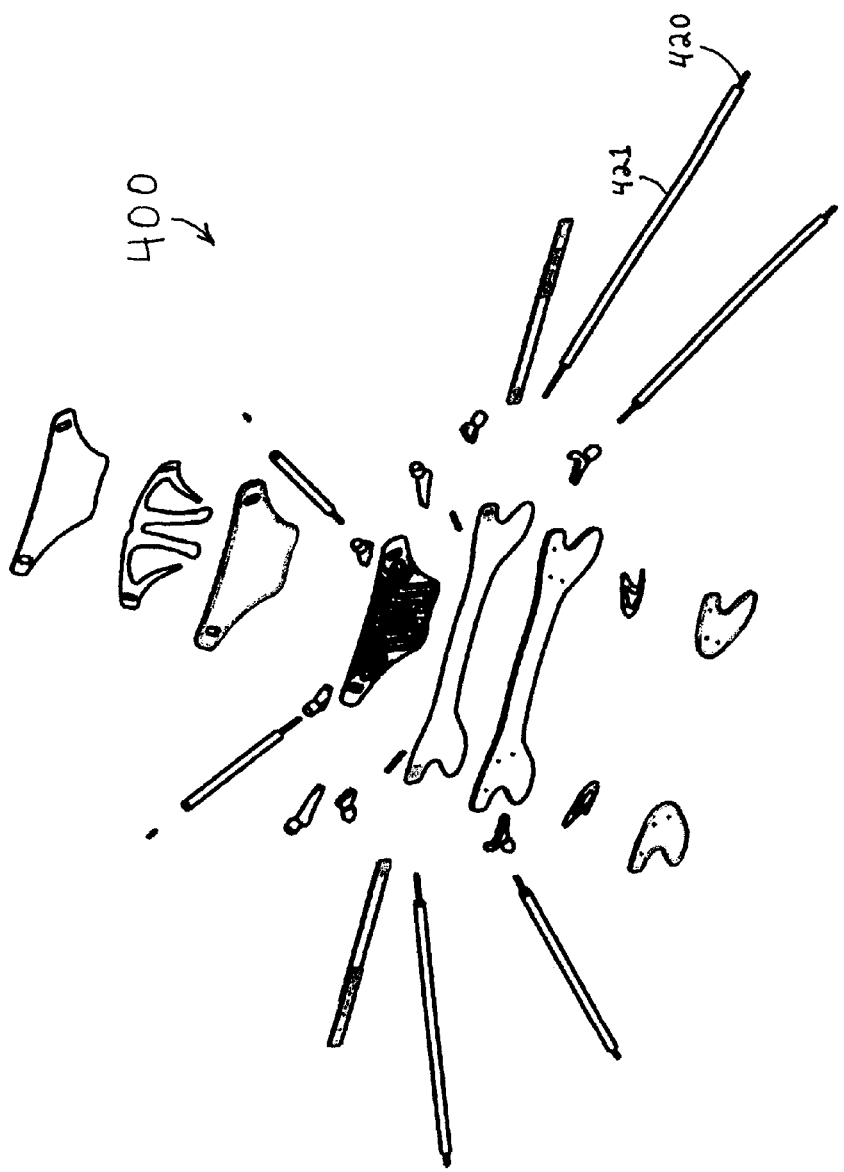

FIG. 12B is an exploded view of the head pad.

Figure 12C:
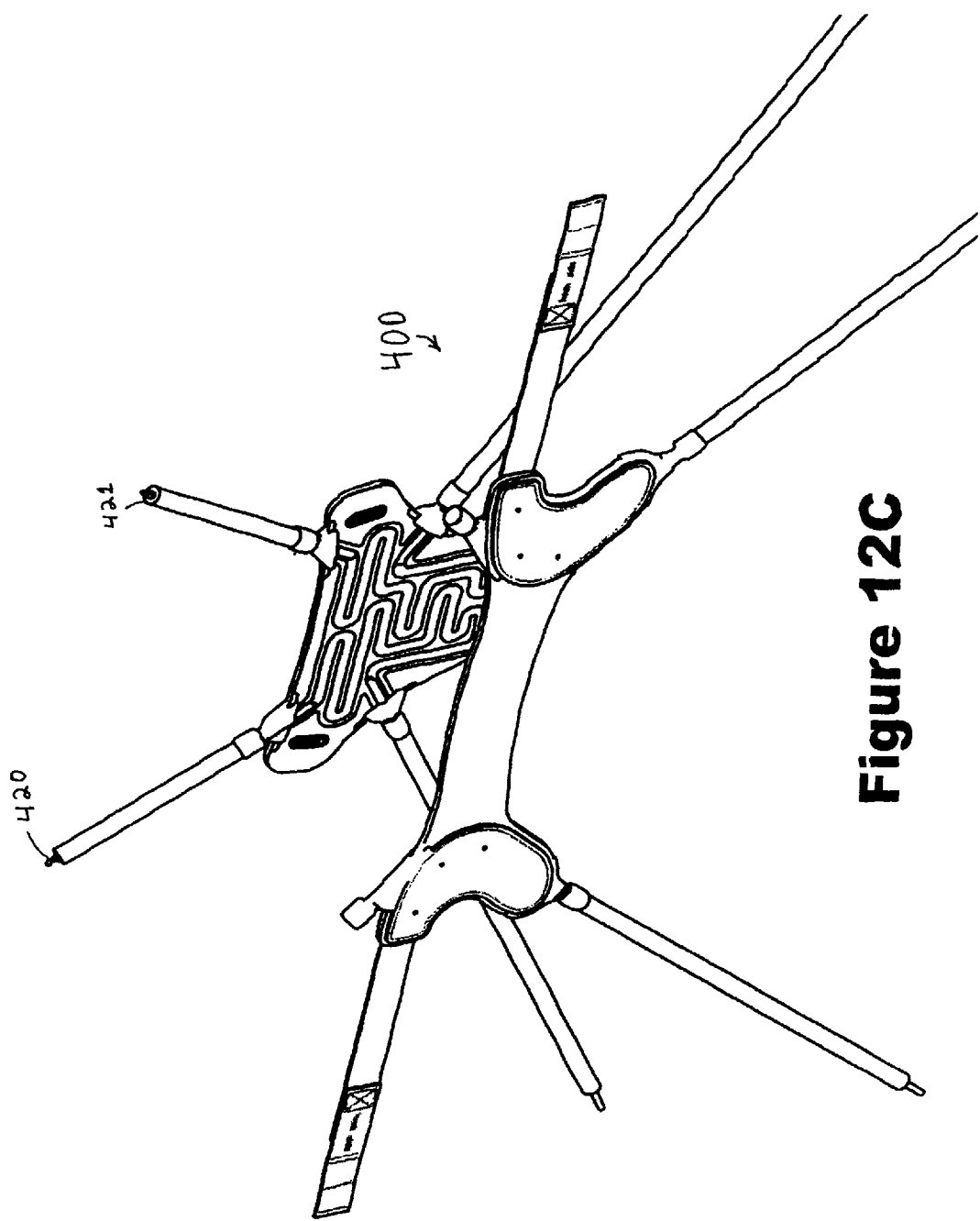

FIG. 12C is a perspective view of the fore pad portion and the rear pad portion of the head pad, these fore/rear pad portions being shown disassembled from each other.

Figure 12D:
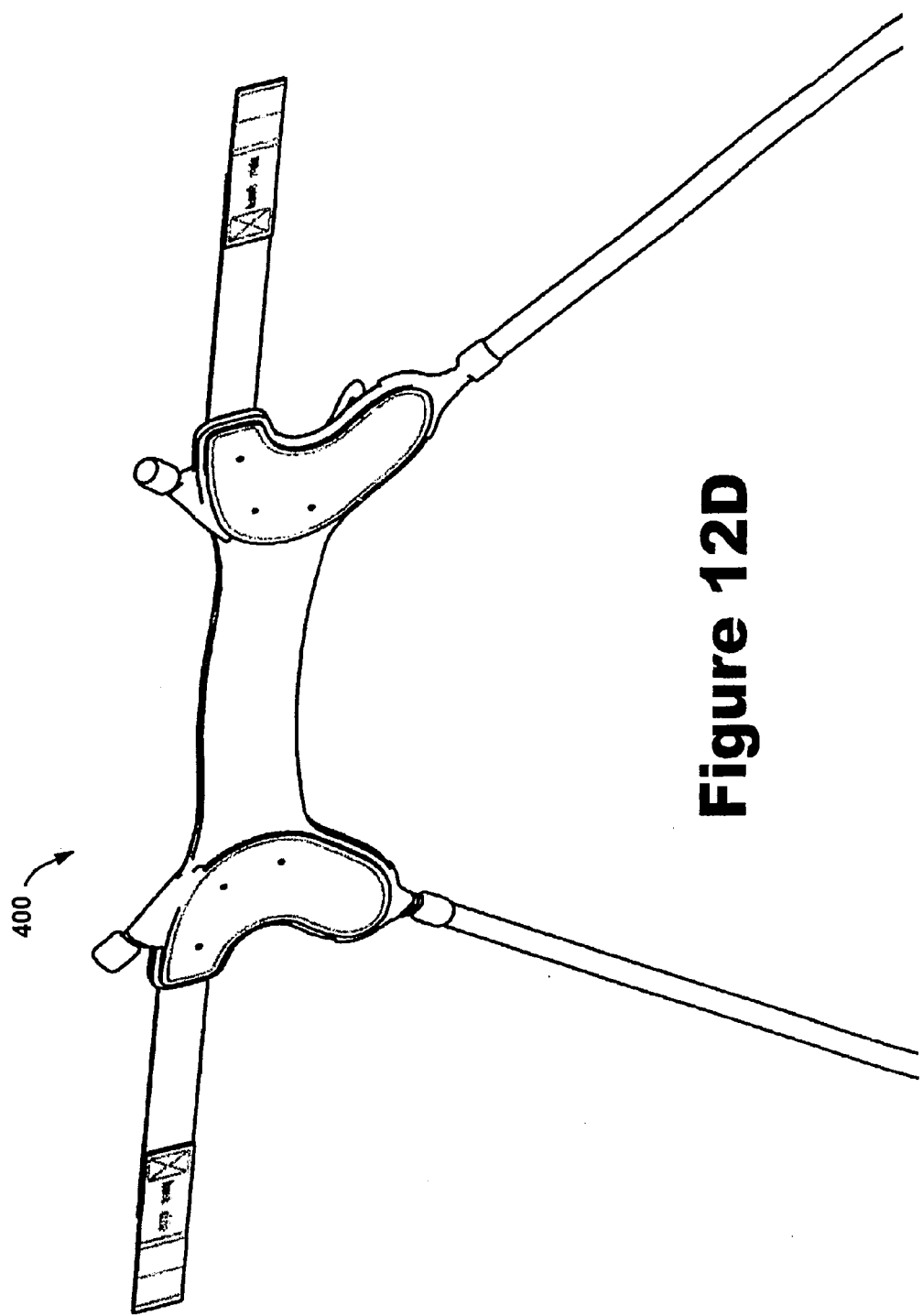

FIG. 12D is an isolated view of the fore pad portion.

Figure 12E:
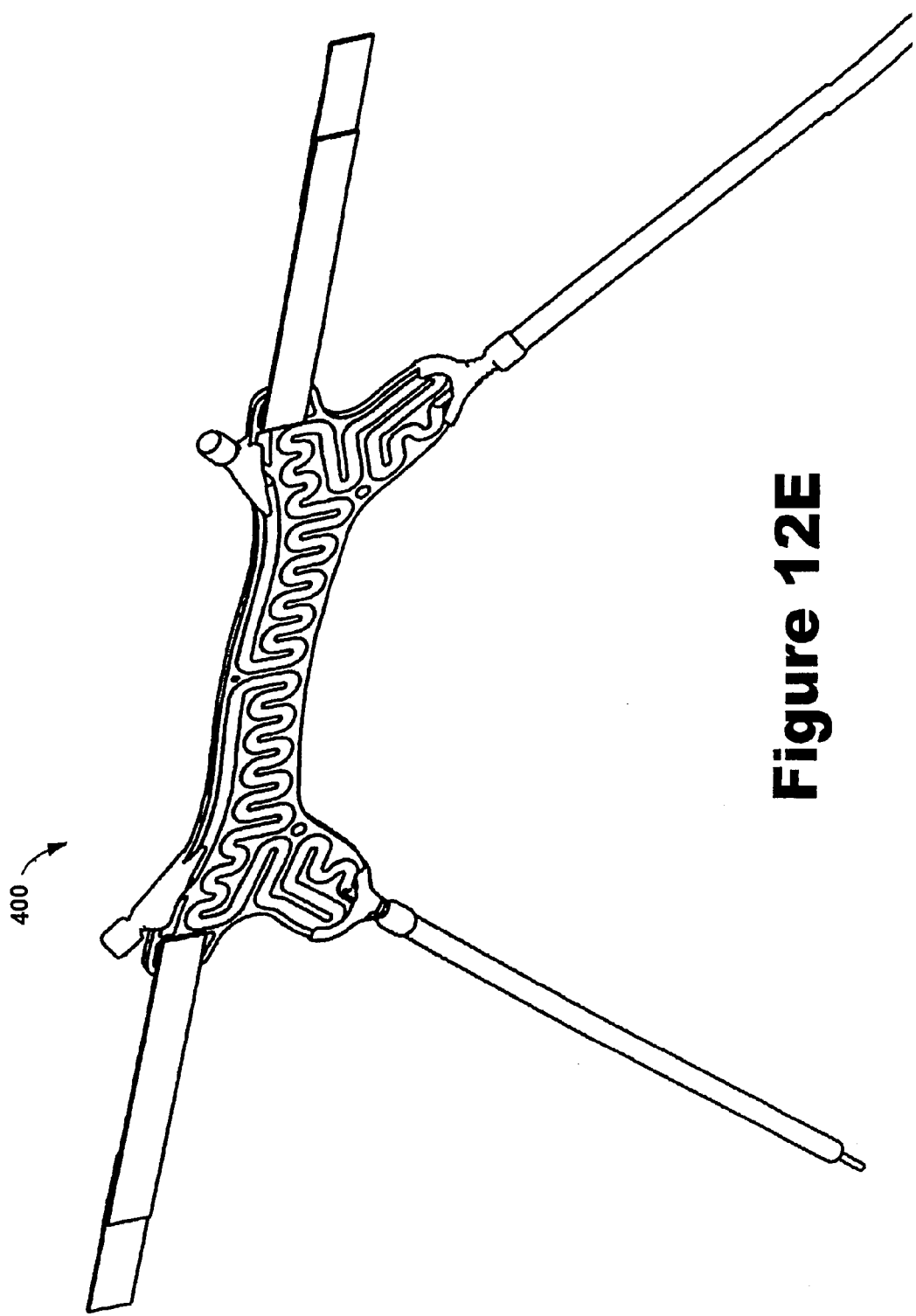

FIG. 12E is an isolated view of the fore pad portion with a layer removed to reveal fluid channels.

Figure 12F:
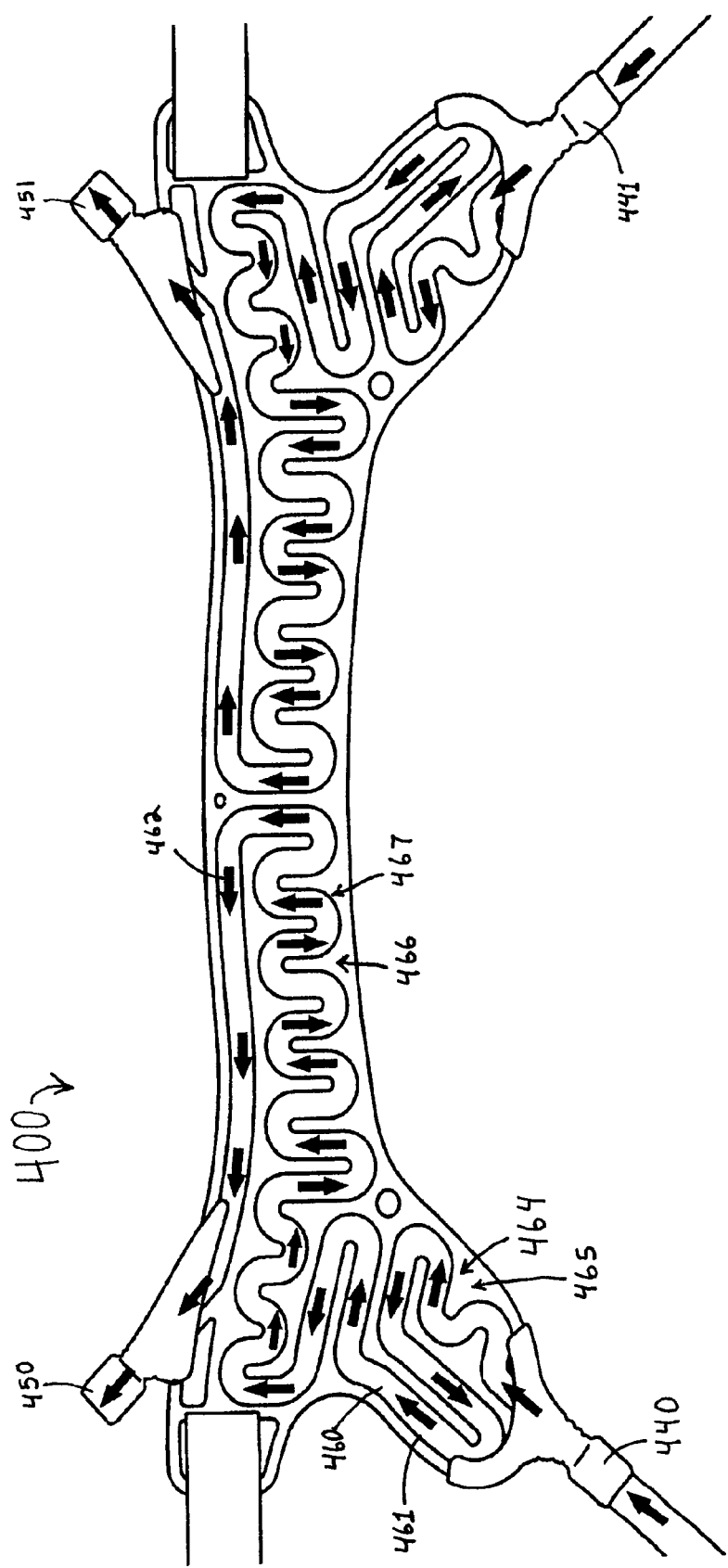

FIG. 12F is an isolated view of the fore pad portion schematically showing flow path through the fluid channels.

Figure 12G:
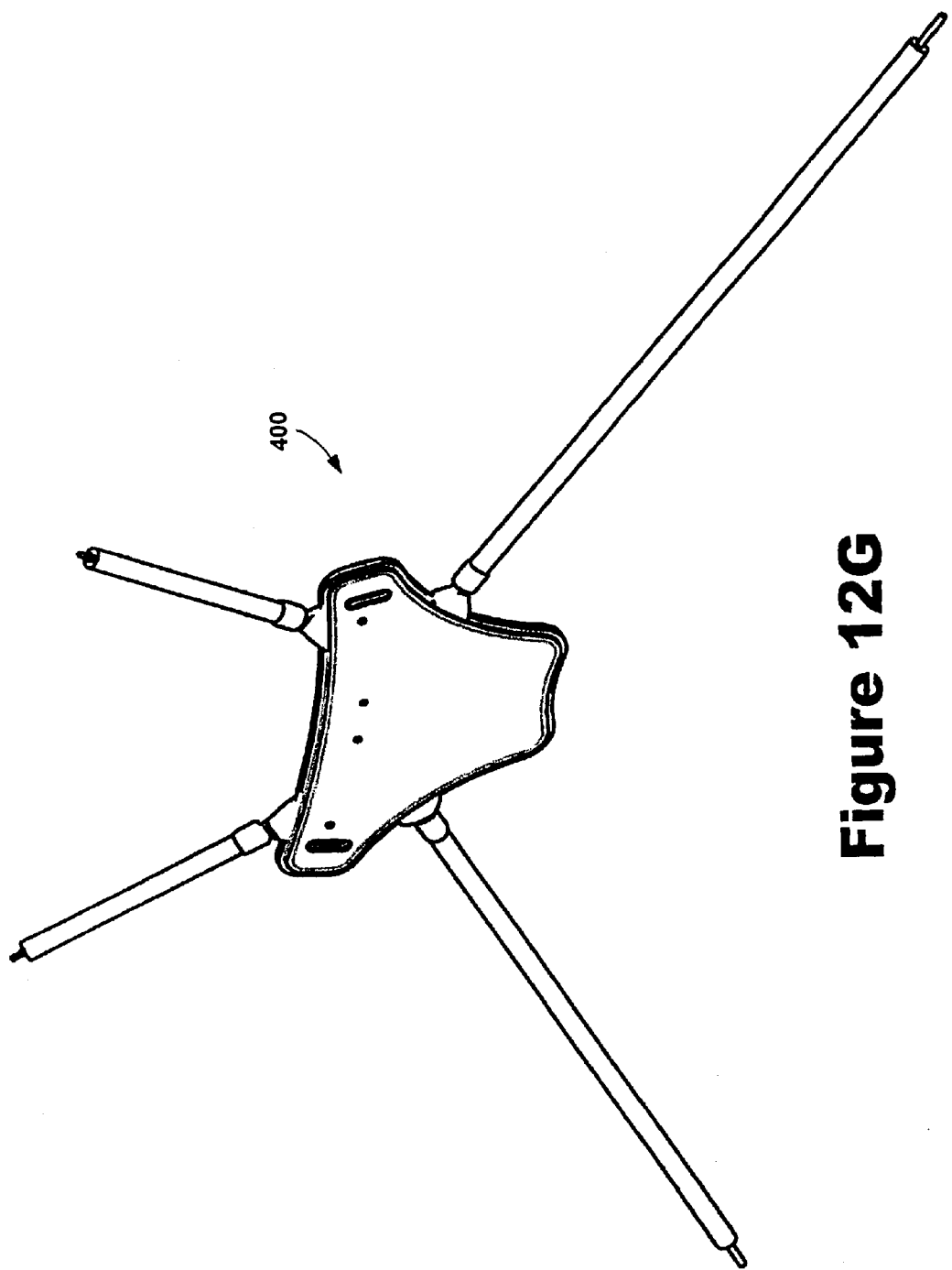

FIG. 12G is an isolated view of the rear pad portion.

Figure 12H:
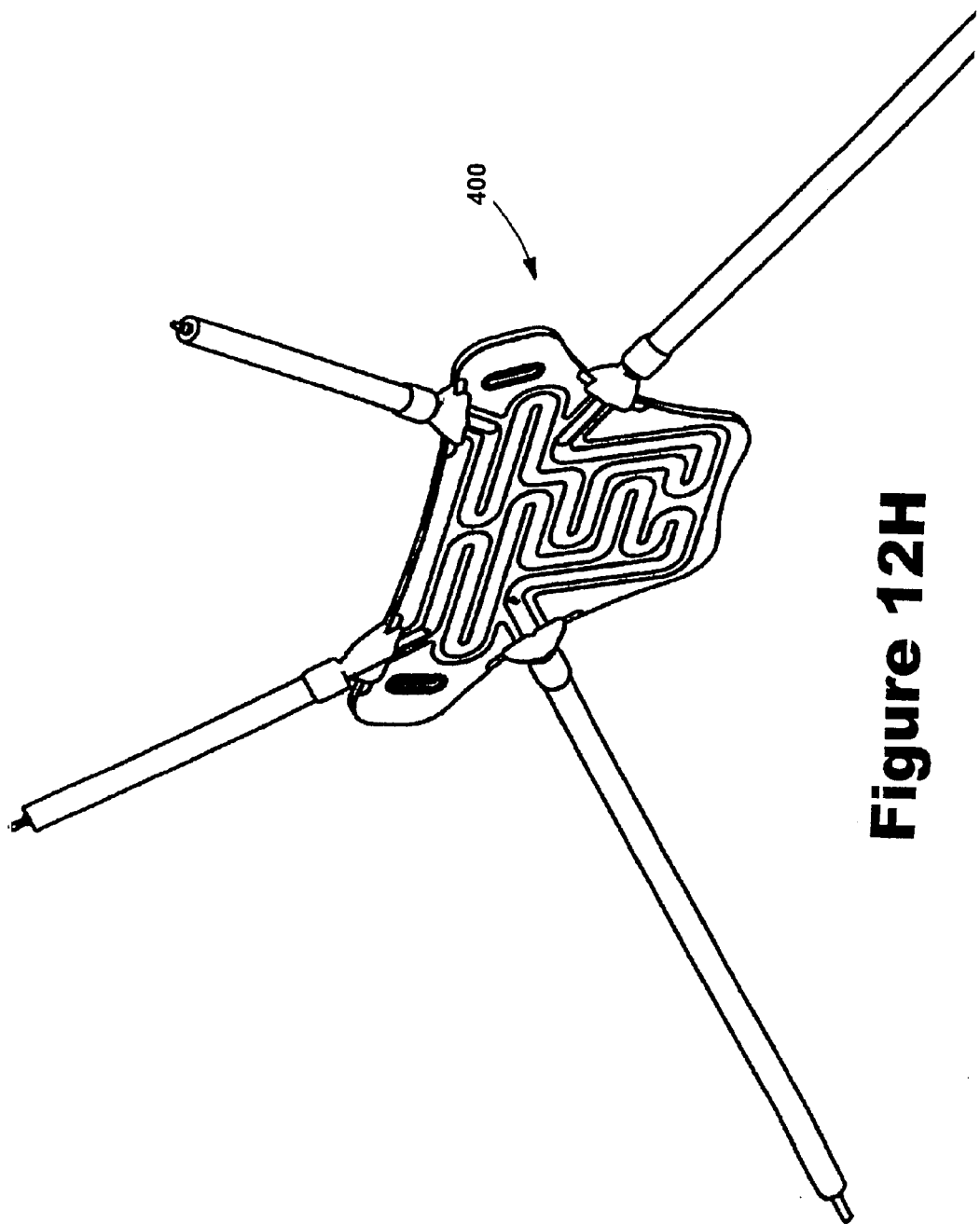

FIG. 12H is an isolated view of the rear pad portion with a layer removed to reveal fluid channels.

Figure 12I:
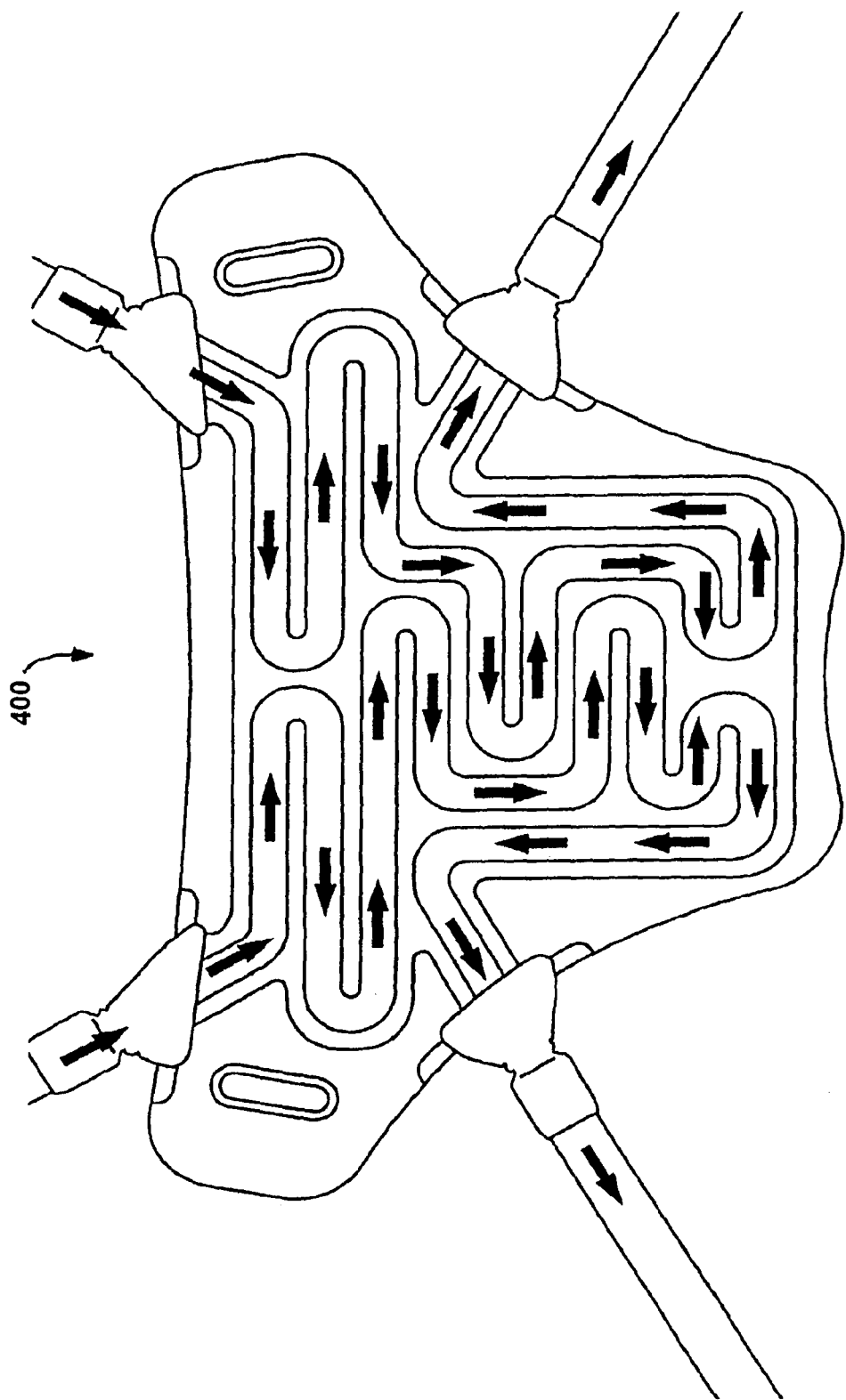

FIG. 12I is an isolated view of the rear pad portion schematically showing flow paths through the fluid channels.

Figure 13A:
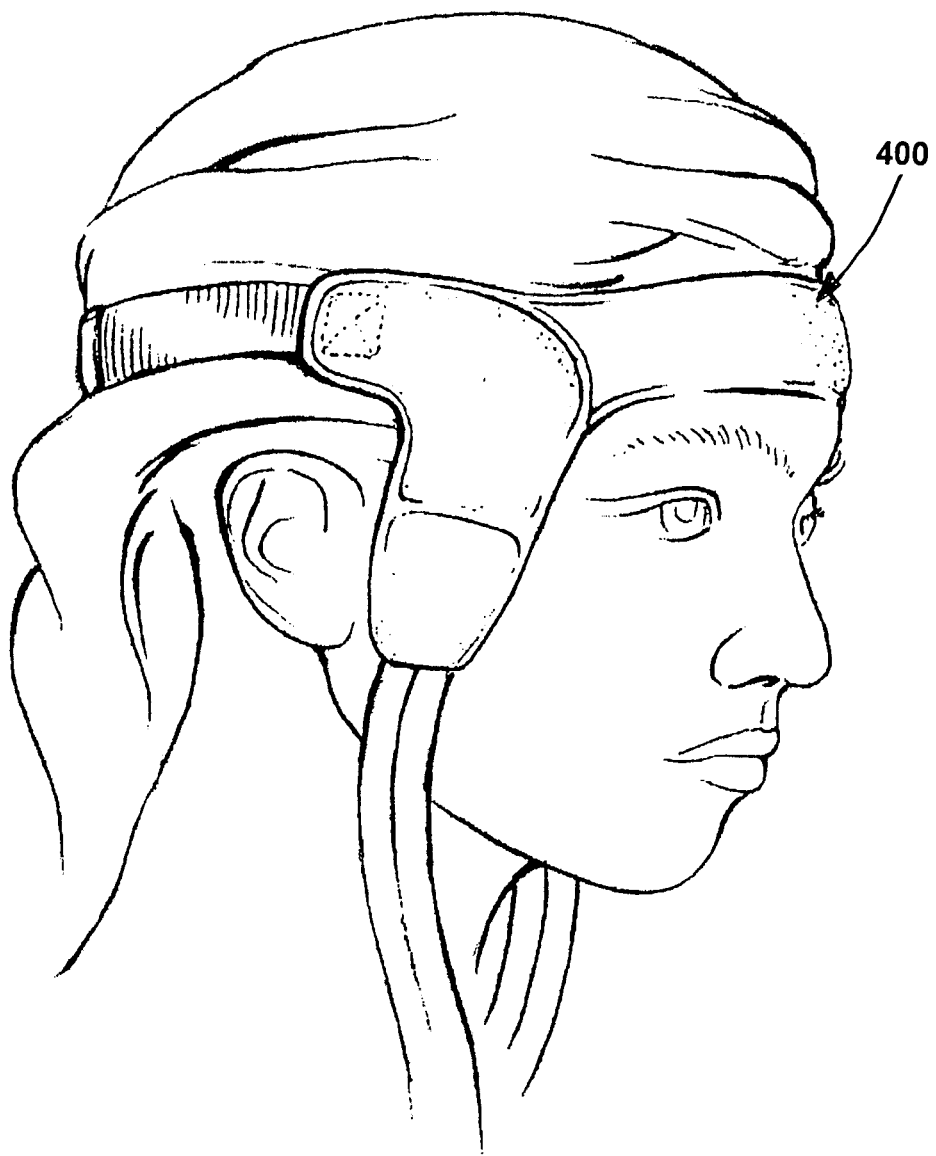

FIG. 13A is a perspective view of a tissue-interacting device wherein the device is a front head pad.

Figure 13B:
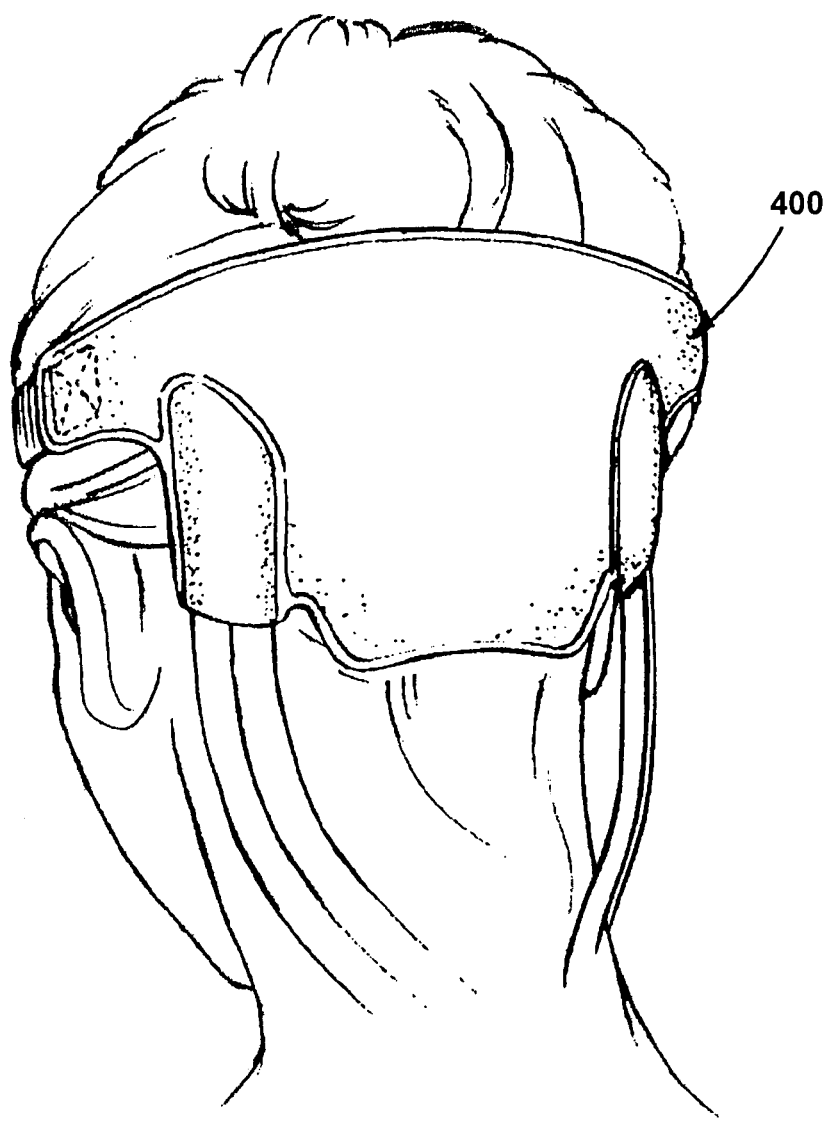

FIG. 13B is a perspective view of a tissue-interacting device wherein the device is a rear head pad.

Figure 14A:
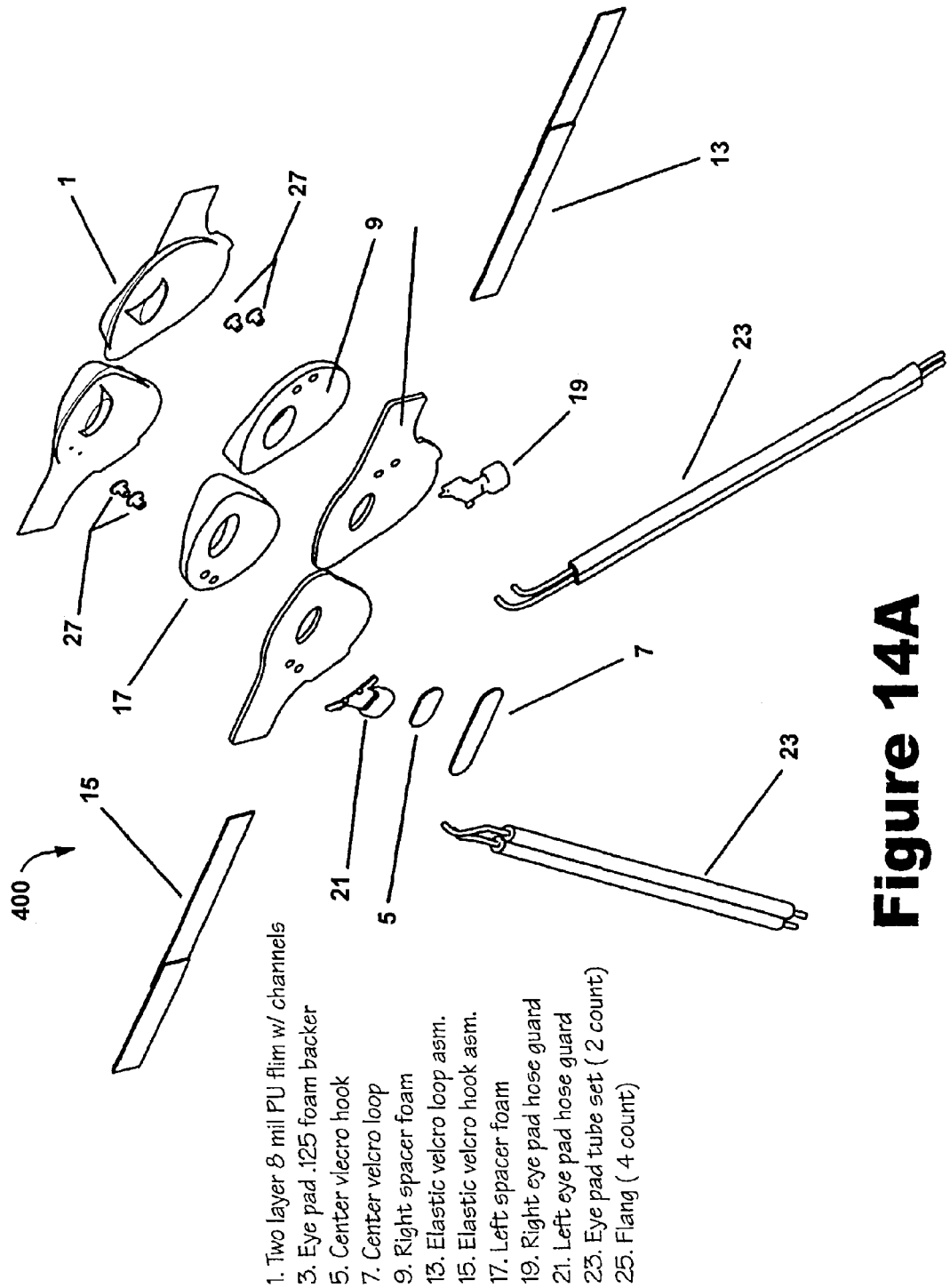

FIG. 14A is an isolated exploded view of the tissue-interacting device wherein the device is an eyepad.

FIG. 14B is an isolated view of the eyepad laid flat on a surface.

Figure 14C:
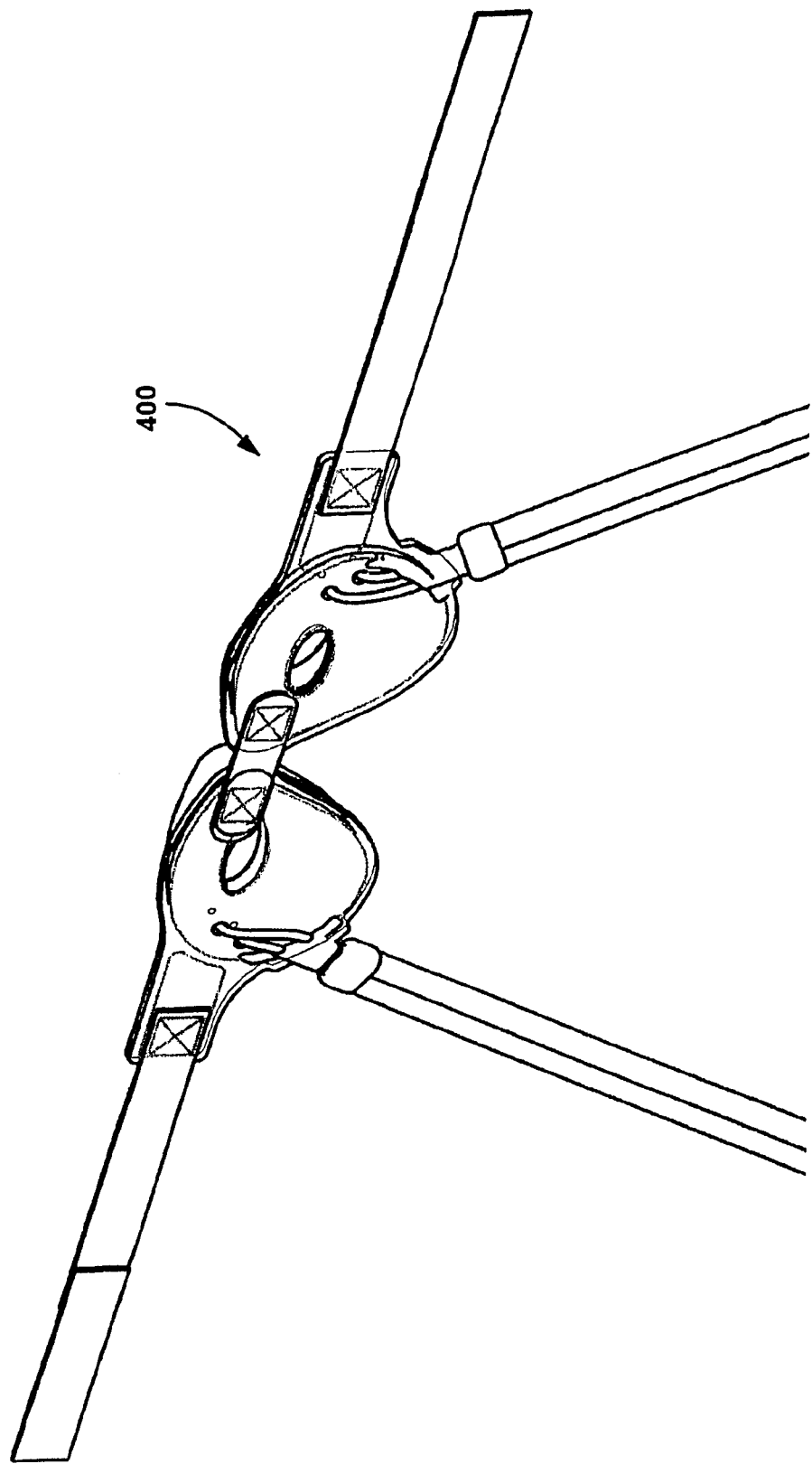

FIG. 14C is an isolated view of the face-remote side of the eyepad.

Figure 14D:
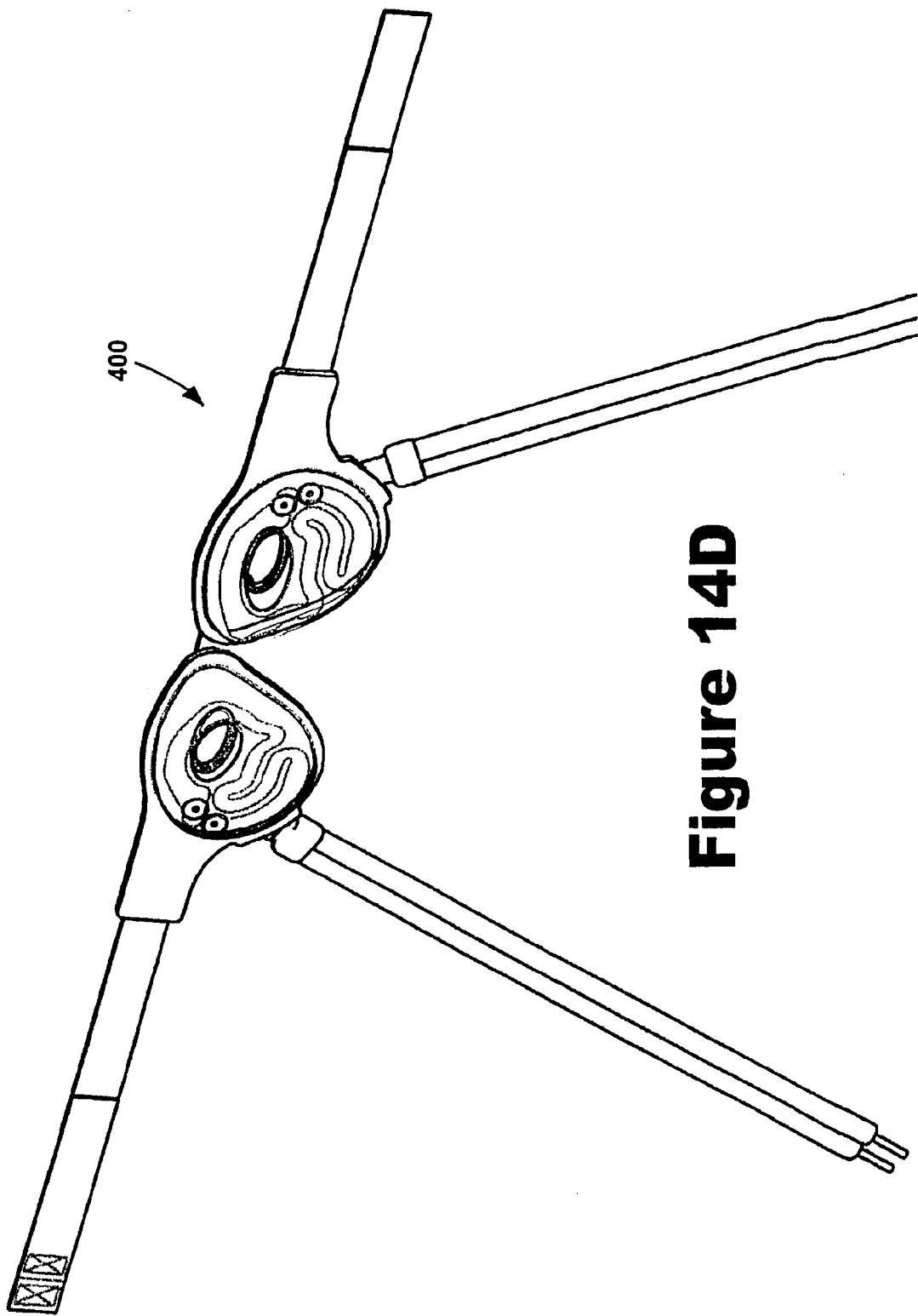

FIG. 14D is an isolated view of the face-adjacent side of the eyepad, with the flow channels being schematically shown in phantom.

Figure 14E:
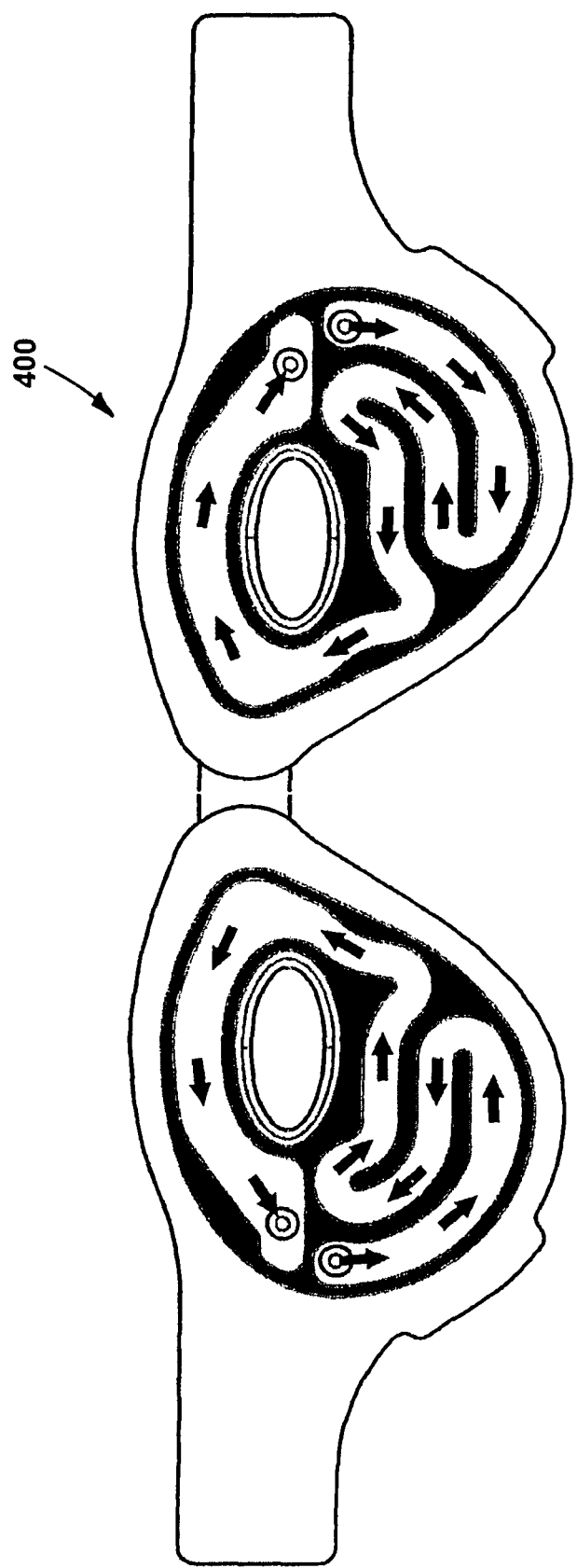

FIG. 14E is an isolated view of the face-remote side of the eyepad, schematically showing flow paths through the fluid channels FIG. 15A is an isolated view of another embodiment of the tissue-interacting device, this device being a rectangular bodypad.

FIG. 15B is an isolated view of the bodypad, with a layer removed to reveal flow channels.

Figure 15C:
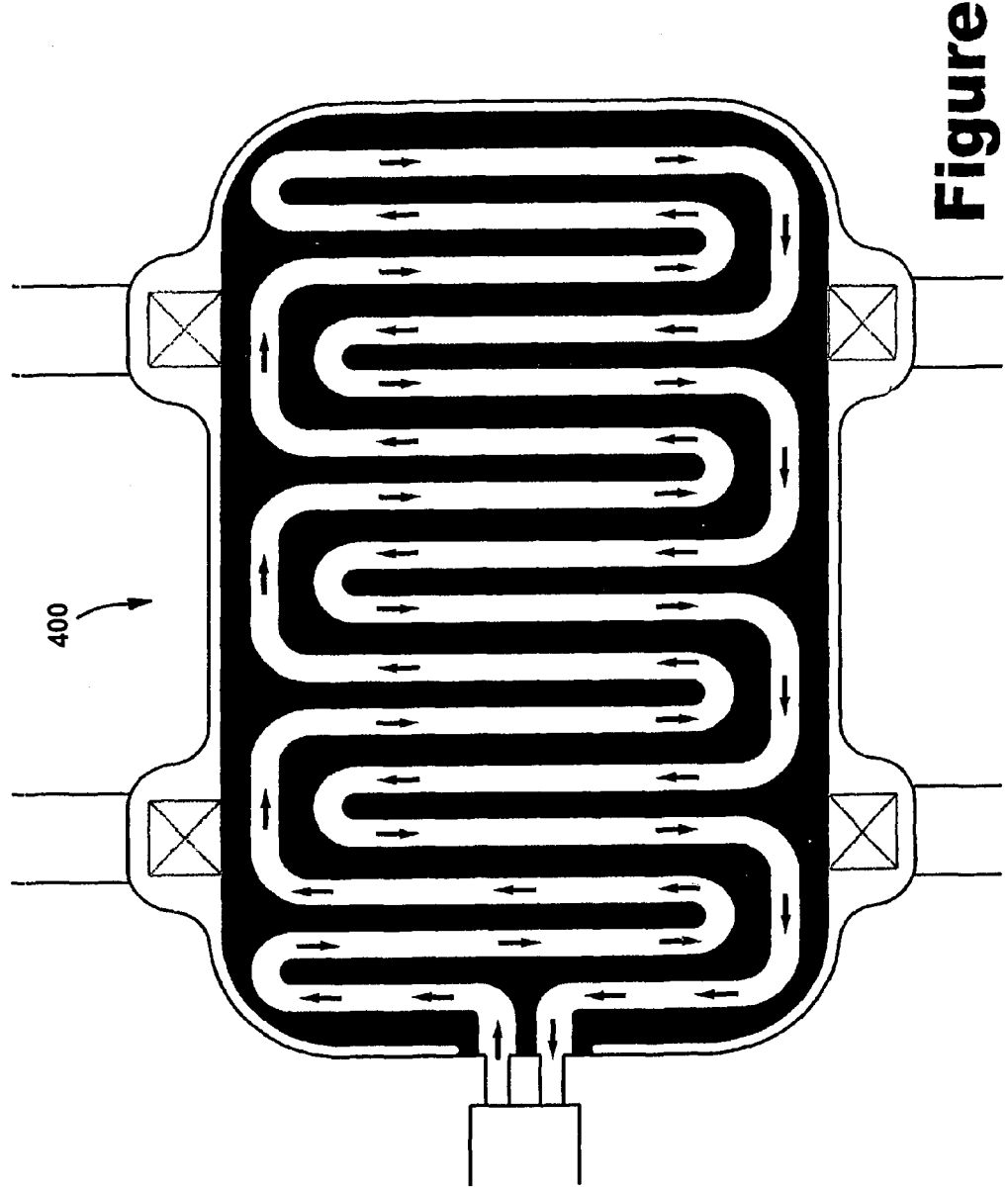

FIG. 15C is an isolated view of the bodypad schematically showing flow paths through the fluid channels.

Figure 16:
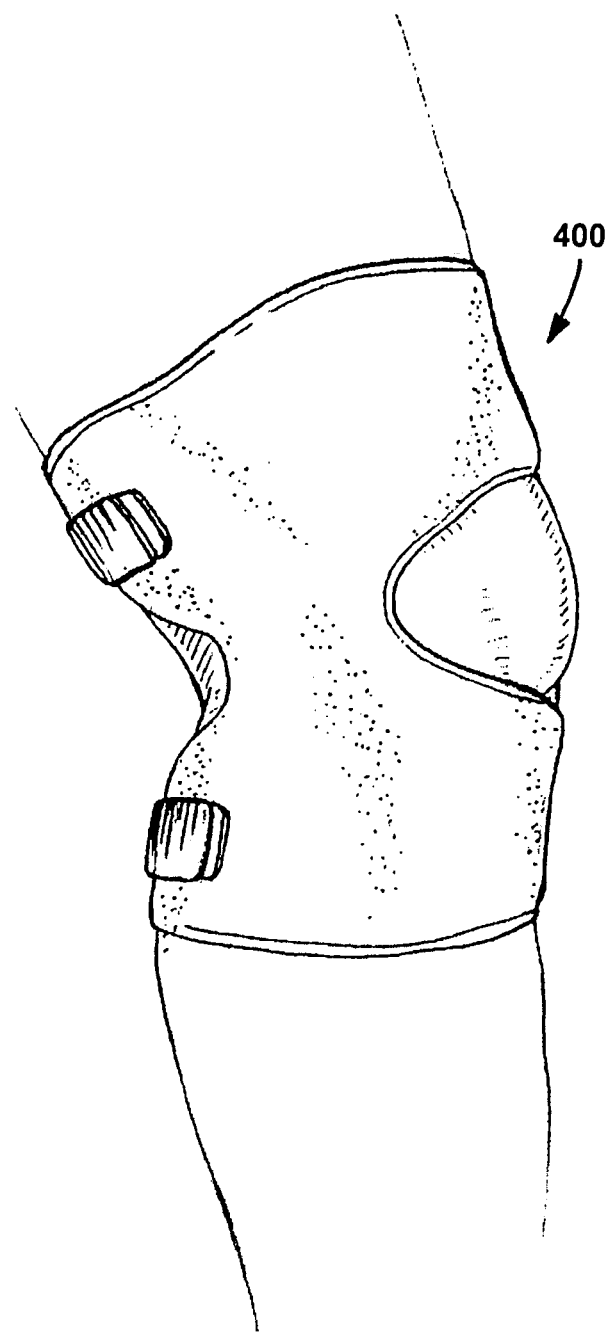

FIG. 16 is a perspective view of a tissue-interacting device in use on the therapy-receiving wearer, this device being a knee pad.

Figure 17:
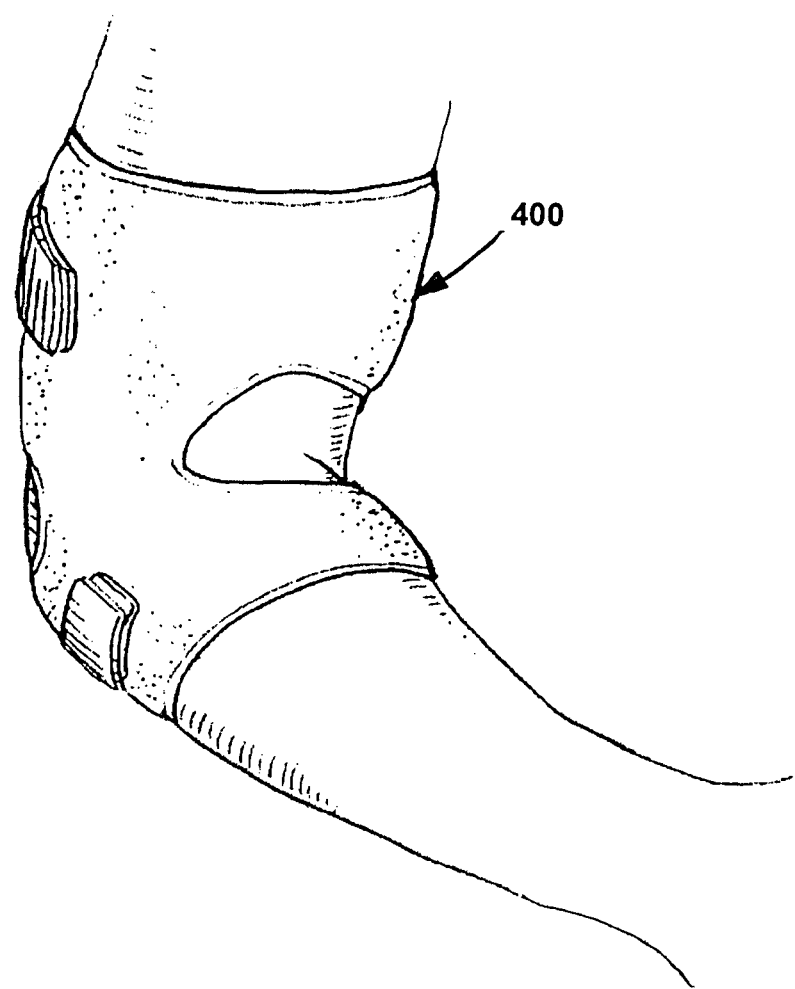

FIG. 17 is a perspective view of a tissue-interacting device in use on the therapy-receiving wearer, this device being an ankle/foot pad.

Figure 18:
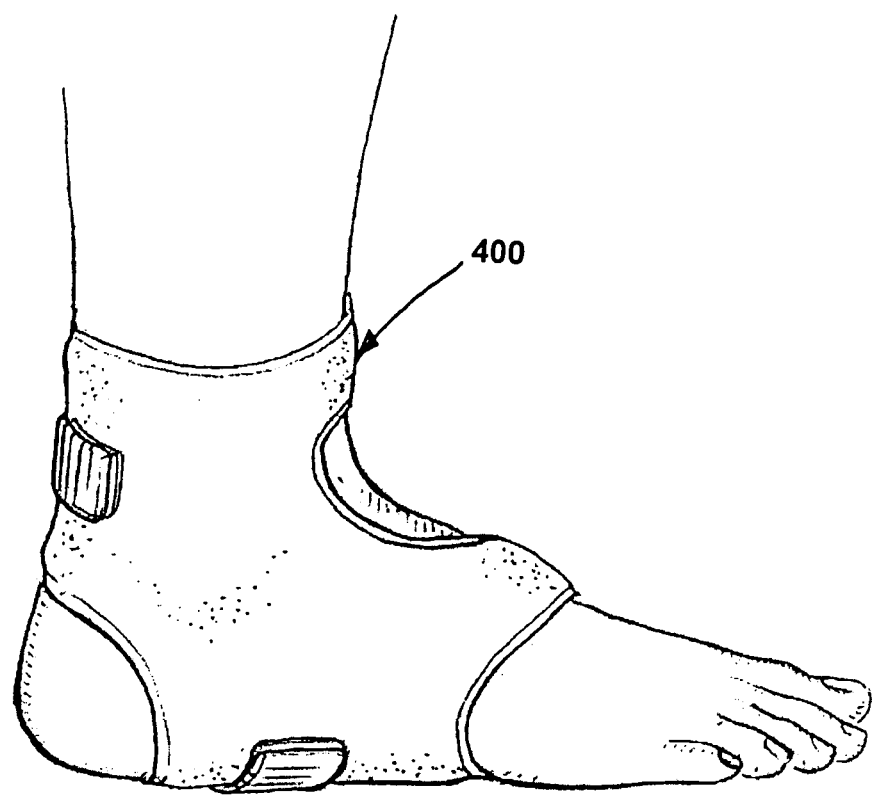

FIG. 18 is a perspective view of a tissue-interacting device in use on the therapy-receiving wearer, this device being an elbow pad.

Figure 19:
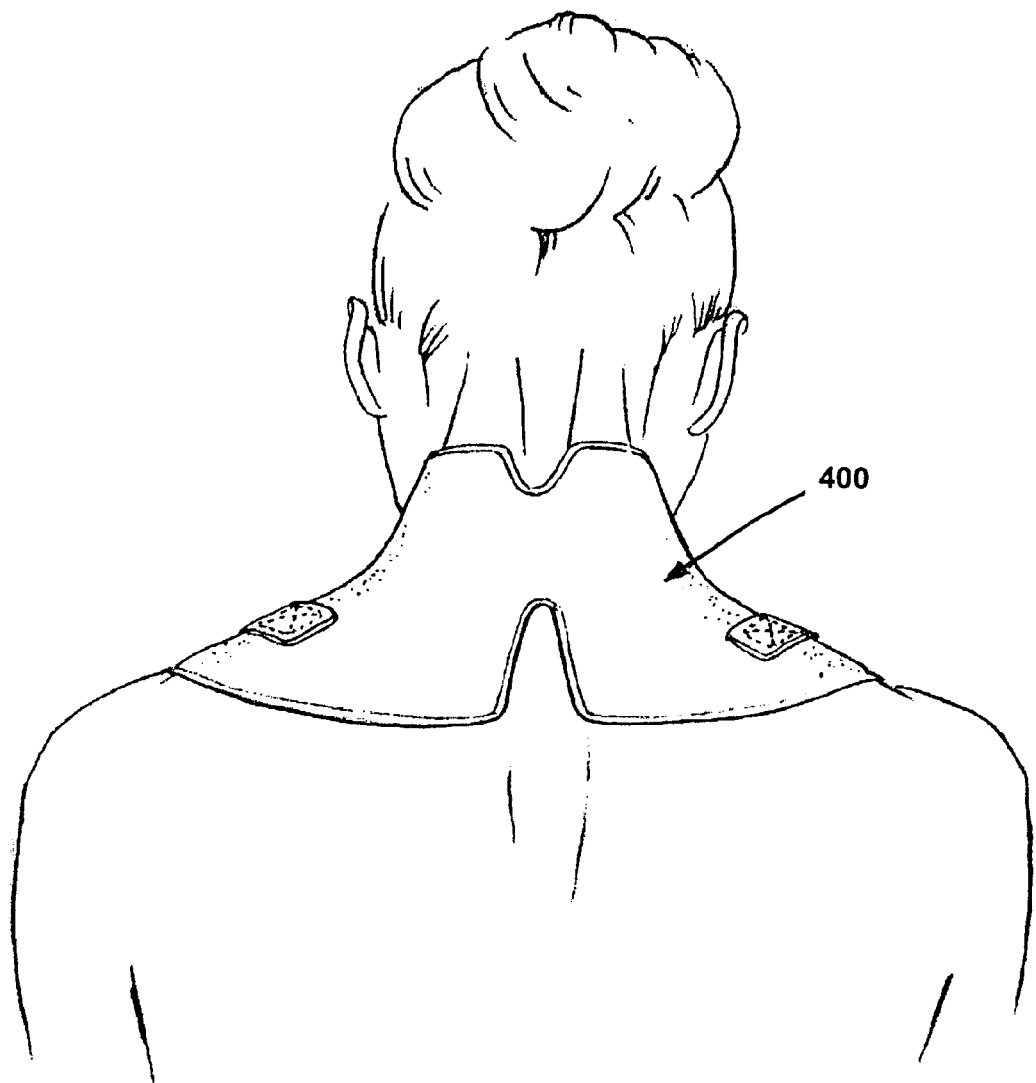

FIG. 19 is a perspective view of a tissue-interacting device in use on the therapy-receiving wearer, this device being a shoulder and neck pad.

SUMMARY

A thermal therapy system is provided wherein the tissue-interacting device targets certain areas whereby thermal therapy is efficiently and effectively delivered. The system and/or device can be manufactured in a cost-effective manner, is easy to use, comfortable, and can have a compact design.

DESCRIPTION

Figure 1:
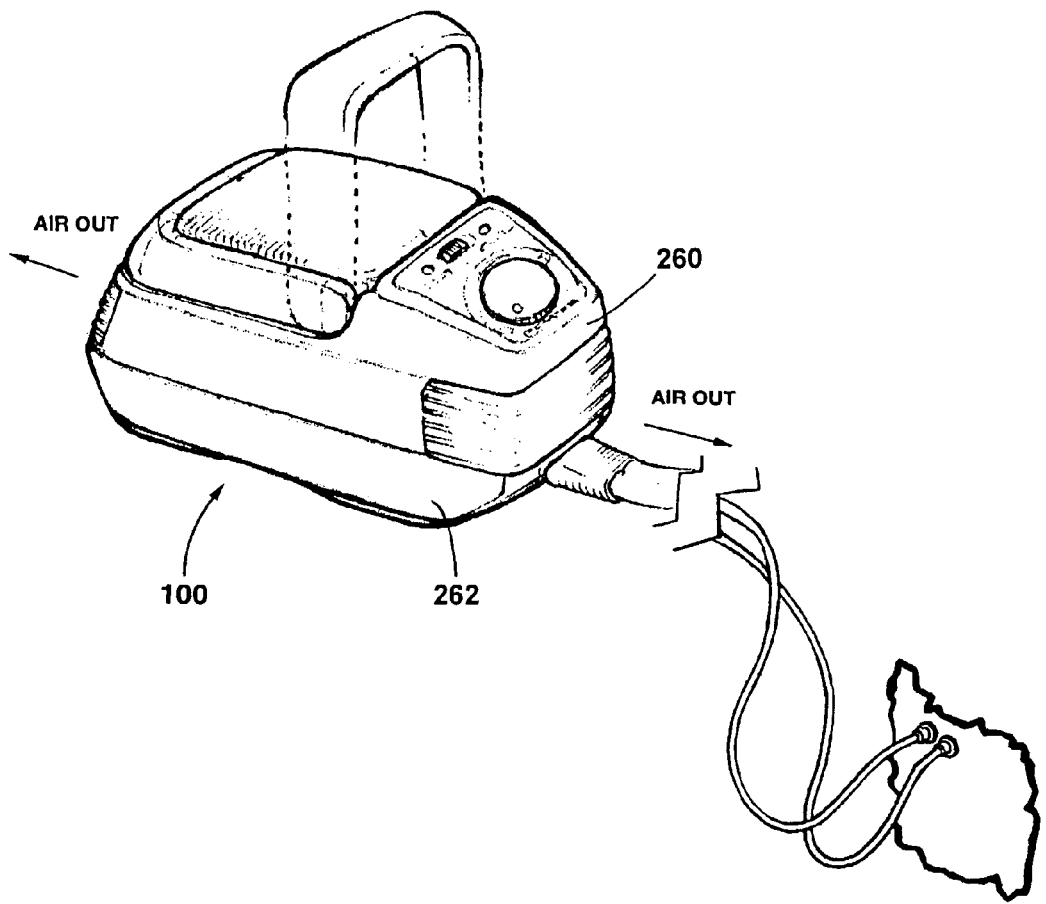
FIG. 1 is a schematic view of a thermal therapy system, the system including a fluid-manipulating device and a tissue-interacting device.

Referring now to the drawings, and initially to FIG. 1, a thermal therapy device 100 is schematically shown. The thermal therapy device 100 comprises a fluid-manipulating device 200, a tissue-interacting device 400, and plumbing establishing fluid circulation paths therebetween. The fluid-manipulating device 200 heats/cools the therapy-providing fluid (e.g., water, oil) and pumps it through fluid channels in the tissue-interacting device 400. The tissue-interacting device 400 is placed in contact with the appropriate areas of the therapy-receiving person's body so that fluid passing through the channels can thermally interact therewith.

Figure 2A:
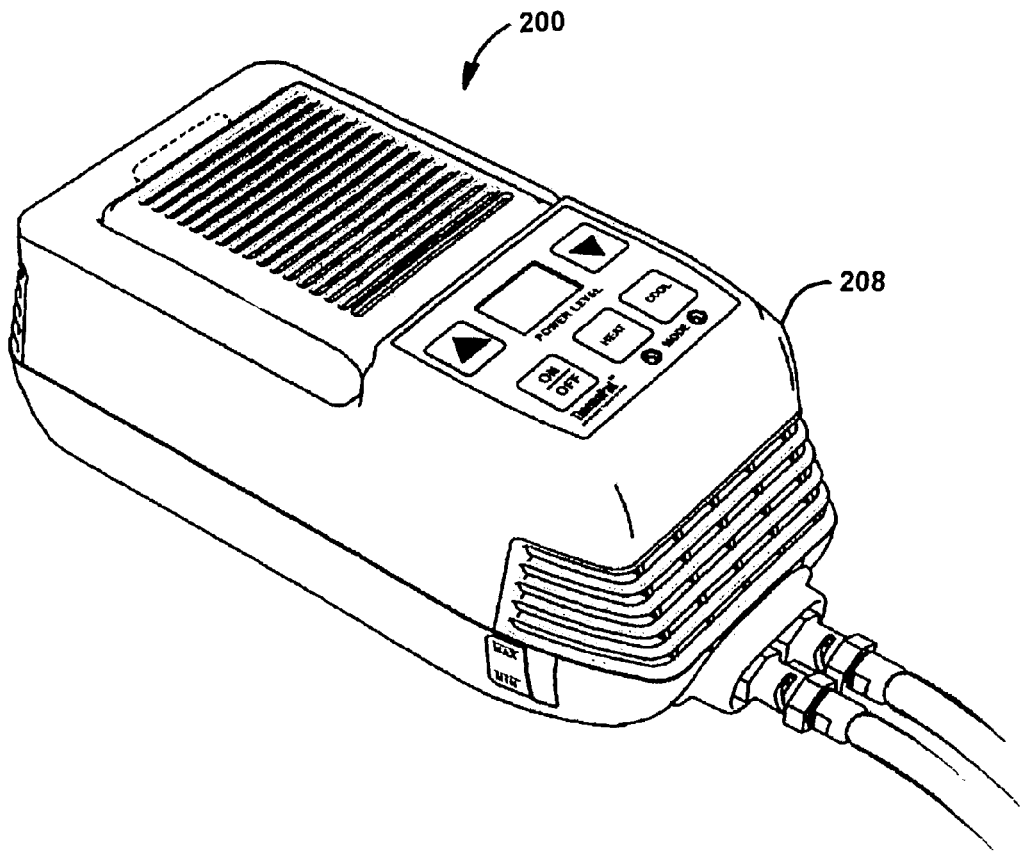
FIG. 2A is a top perspective view of the fluid-manipulating device.
Figure 2B:
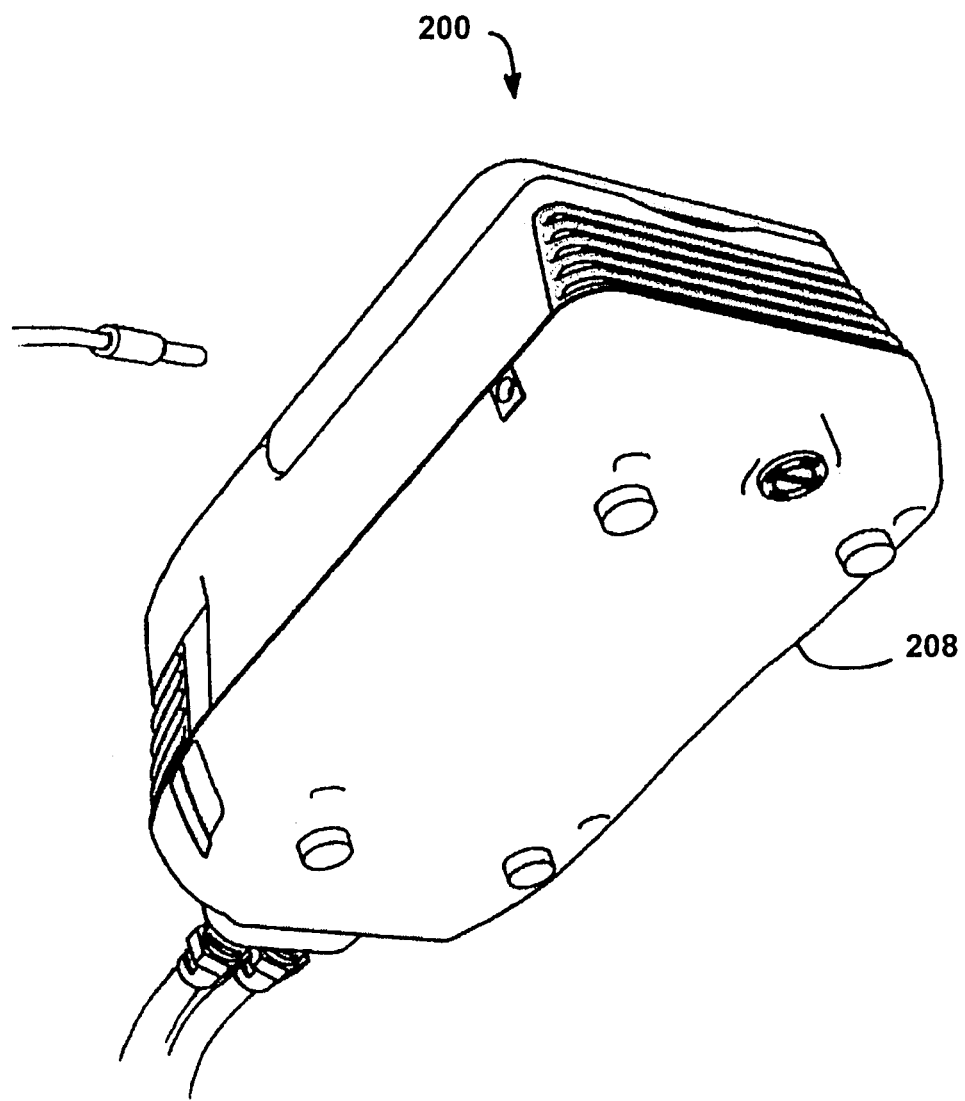
FIG. 2B is a bottom perspective view of the fluid-manipulating device.
Figure 3:
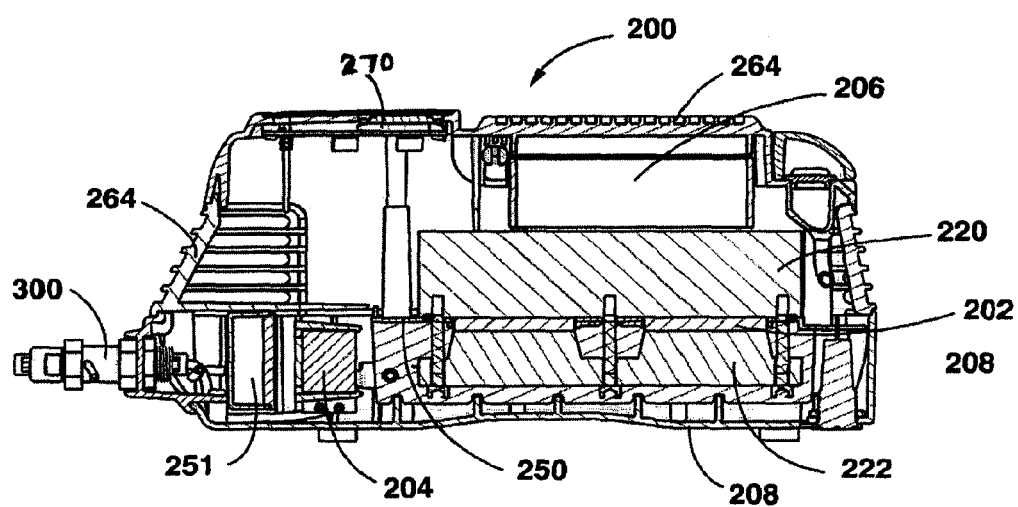
FIG. 3 is a full cross sectional view of the fluid-manipulating device.
Figure 4A:
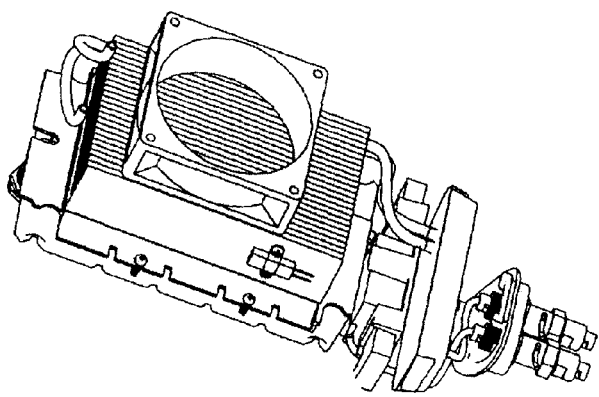
FIGS. 4A and 4B are top and bottom schematic views, respectively, of the fluid-manipulating device without the outer housing components.
Figure 4B:
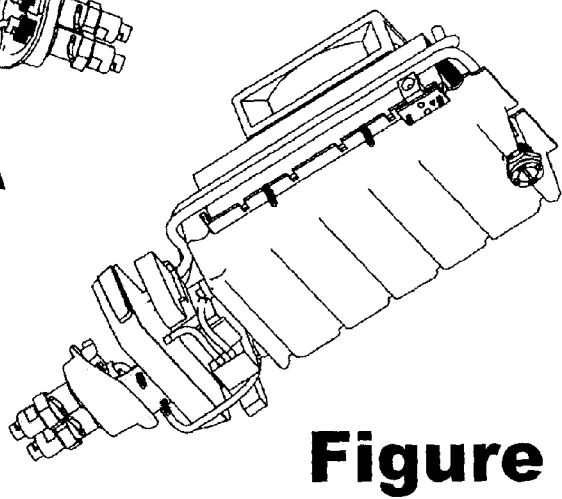

Turning now to FIGS. 2-4, the fluid-manipulating device 200 is shown. The device 200 can comprise a heat exchanger 202, a pump 204, a fan 206, and a housing 208 enclosing these components. The heat exchanger 202 heats/cools the therapy-providing fluid, and the pump 204 circulates the therapy-providing fluid through the system 100. The fan 206 interacts with the heat exchanger's heat sink (sink 220, introduced below). The fluid-manipulating device 200 can be powered by direct 12 v (e.g. car power adaptor) or via a AC/DC converter. Alternatively, the device could be powered by a battery pack (either single use or rechargeable).

The heat exchanger 202 (shown in detail in FIGS. 5A, 5B and 5C) can comprise a heat sink 220, a fluid-passthrough portion 222 (e.g., a block or a cold plate), and thermoelectric module(s) 224 (e.g., Peltier devices).

In FIG. 5A, the fluid-passthrough portion 222 is a block screwed secured to the heat sink 220 (e.g., with screws 230) with the thermoelectric modules 224 situated therebetween. Clamp bars 232 can be used. The block 222 comprises flow passages therethrough which form part of the fluid circulation path. The block 222 can be formed by two block portions 234 and 236, and a gasket 238 therebetween. On or both of the block portions 234/236 can have channels 240 which are part of the recirculation path for the therapy-providing fluid. The channels 240 can be formed by the cut grooves alone, or could be formed by tubing (e.g., copper tubing) inserted therein. The block portions 234/236 are clamped together via several screws (not shown) and may be fabricated from any thermally conducting material. Insulation 242 may be provided.

In the heat exchanger 202 shown in FIG. 5B and the heat exchanger 202 shown in FIG. 5C, the fluid-passthrough portion 222 comprises a cold plate 244 die cast around copper tubing 246 (e.g. in a serpentine configuration) that creates the channels 240. Spacers 248 can be situated between the thermoelectric modules 224 to act as insulation pads when fluid-manipulating device 200 is operating in the cooling mode. The spacers 248 can be separate elements (FIG. 5B) or they can be integrally formed with the passthrough portion 222 (FIG. 5C). In either or any event, the thermoelectric modules 224 interface with the heat sink 220.

The heat exchanger 202 can further comprise a mounting plate 250 and a gasket 252 forming a seal around the thermoelectric modules 224. Machine screws 230, passing through clearance holes in the cold plate 244 can fasten these components. Components are clamped together under pressure, and the machine screws fastened into aligning tapped holes in the heat sink 220. The mounting plate is fastened to the outer periphery of the heat sink 220 and screws the heat exchanger 202 to the housing 208.

The passthrough portion 222 and thermoelectric modules 224 may be insulated using polystyrene, polyurethane, or similar insulating material. These materials may be pre-cut to shape, formed to shape, or poured/molded directly in place. Thermal grease may be used on the tops/bottoms of the thermoelectric modules 224 to ensure good contact with other heat-exchanger components and thereby insure efficient temperature conductivity The heat exchanger, via user controlled switches and/or dials, will be able to operate in either cold or hot mode. When in cold mode, the surface of the thermoelectric device in contact with the block will be cold. By changing polarity, the device can switch to hot mode which results in the surface of the thermoelectric device in contact with the block to become hot. Optionally, an electrical control 270 could be introduced that prevents the user from instantly switching polarity, e.g., if the user activates the polarity switch, power to the devices will be turned off for five minutes to allow the system temperature to acclimate more closely to ambient before turning the power back on. This type of control will prevent the devices from being shocked by rapid and dramatic swings in temperature. Optionally, electrical controls 270 could be introduced that limit the temperature that the liquid can achieve. This could include a high temperature and/or low temperature control. Moreover, regardless of the mode of operation, the user may be able to control the intensity of the temperature via a control on the housing. The device may optionally include controls 270 to maintain specific temperature ranges. Additionally, an LCD readout could be incorporated to display data such as actual temperature, desired temperature, etc.

It should be noted that while thermoelectric elements have been shown and described as an appropriate means for thermally manipulating the therapy-providing fluid, other heating/cooling means are certainly possible and contemplated.

The flow rate produced by the pump 204 may be pre-set or user controlled to achieve varying temperature ranges. The type of pump used may be a diaphragm pump, peristaltic pump, etc. In order to control the flow rate, a regulating valve connected to the pump may be used.

The fan 206 can be placed in direct contact with the heat sink and configured to direct airflow into the heat sink or to pull air away from heat sink, depending upon the desired thermal conditions.

Optionally, a reservoir 251 could be incorporated into the system 100. (See FIG. 3.) This reservoir 251 could be cooled and/or heated using additional thermoelectric devices 224 or could be used to simply hold fluid before or after it is passed through the block/plate 222. The reservoir 251 can be comprised of a body and lid portion, joined together by ultrasonic weld or solvent to form a leak-proof vessel. The sides of the reservoir body fit into receiving slots in the housing 208, positioning the reservoir within. Two lengths of tubing to fill the reservoir fit over protrusions in the reservoir lid portion and extend rearward to connect to the fill port detail integral to the top housing. One of these lengths provides a conduit for fluid to enter into the reservoir, while the other provides a conduit for air to exit out from the reservoir. A urethane rubber fill cap creates a watertight seal over the fill port when not in use. A length of tubing connects to a further protrusion in the reservoir lid and serves as the fluid supply conduit to the diaphragm pump.

The pump 204 snaps into a pump carrier that includes pre-assembled flexible foam inserts located on each side that slide into receiving ribs in the bottom housing. The foam inserts suspend the pump carrier within the housing and keep it from coming into contact with and transferring pump vibration to any other internal components. Another length of tubing connects the fluid exit connection on the pump to a fitting going into the cold plate of the heat exchanger. Another length of tubing is attached to a fluid exit fitting on the cold plate and to the fluid exit coupling assembly, completing the loop through the fluid-manipulating device.

The housing 208 can include a top portion 260 and a bottom portion 262. Vents 264 (e.g., slats, screens, etc.) can be provided to permit air to be pulled into the fan 206 and then expelled as it blows across the heat sink 220. For example, as illustrated, air is pulled into the housing via top vents and expelled via side vents, but any compatible air path may be used.

As shown in FIG. 3, side vents can be trapped between the housing portions 260/262. A PCB is fastened to the underside of the top housing and includes a LCD used to operate the device. The window of the LCD aligns with an opening in the top housing and a read through window in the affixed membrane switch. Headers located on the bottom face of the PCB receive plugs with leads to all electrical components within the device providing easy assembly. A temperature sensor is also incorporated into the PCB, and provides a means by which to regulate the system performance in both heating and cooling modes to keep tissue-interacting devices from becoming too hot or too cold. An additional electronic function designed into the PCB is an automatic power delay when switching from one mode to the other. This protects the thermoelectric devices from degradation that otherwise may occur when switching polarities too quickly, the means by which one mode changes to the other. A plastic handle features protruding side clips that snap assemble to the outside of the top housing and provide a fulcrum point at which the handle can swing up vertically for carrying the device.

FIGS. 6A and 6B show a coupling assembly 300 with a body portion 302 and an insert portion 304 attached and disconnected, respectively. The body portion 302 the coupling is fastened to the coupling mount with the panel mount nut. Upon disconnection, the insert portion of the coupling is rotated 90° counter clockwise as integral locking pins follow angled slots in the body half. At the end of the turn, openings at the top end of the slots allow for extraction of the locking pins and separation of the coupling assembly.

FIGS. 7 and 8 show a coupling assembly 300 wherein the portions 302/304 have feature internal valves that shut of flow when they are disconnected. Valve stems in both halves are made to receive sealing o-rings and rearward compression springs that bias the o-rings to seat and seal when coupling halves 302/304 are separated. Upon connecting the coupling halves 302/304, the front end of each valve stem come in contact with one another, compressing the springs and releasing the o-ring seal, allowing flow of fluid. An exterior o-ring positioned over the insert seals the two halves when together to prevent leaking. Barb fittings on both outside ends of the coupling insert and body halves receive tubing leading to the interior workings of the fluid-manipulating device and tissue-interacting devices. As shown in the Figures depicting the tissue interacting devices (in particular, FIGS. 12B and 12C), the tubing 420 may be radially enclosed in a layer of material 421 for insulating the tubing.

FIGS. 9A and 9B show a coupling assembly 300 wherein both the fluid enter and fluid exit connections are incorporated into one insert half 304 and one body half 302, allowing for the quick disconnection of both in one step as opposed to two. The coupling insert half 304 features protrusions with clip details that are received by corresponding pockets in the coupling body 302. To disconnect the coupling halves 302/304, the clip details on these protrusions are squeezed inward on each side simultaneously, and the halves 302/304 allowed to release from each other.

The portions 302/304 can have internal valves with shut off flow upon disconnection. (FIGS. 10-11.) Valve stems in both halves 302/304 are made to receive tapered rubber seals and rearward compression springs that bias the seals to seat and seal when coupling halves 302/304 are separated. Upon connecting the coupling halves 302/304, the front end of each valve stem come in contact with one another, compressing the springs and releasing the rubber seal, allowing flow of fluid. An exterior o-ring positioned over the coupling insert 304 and interior o-rings positioned within the coupling body 302 seals the two halves 302/304 when together to prevent leaking. Barb fittings on both outside ends of the coupling insert 304 and body 302 halves receive tubing leading to the interior workings of the fluid-manipulating device 200 and tissue-interacting devices 400.

Referring now to FIGS. 12A-12I, they show the tissue-interacting device 400 as a head pad specifically designed to deliver thermal therapy to three of the known trigger point areas for migraines. This includes the forehead area, the occipital area, and the temporomandibular joint (TMJ). The head pad can also be used for relief of tension headaches, focused TMJ pain, and for general relaxation. In the illustrated embodiment, a fore pad portion interacts with the forehead area and the TMJ areas (see FIGS. 12D-12F) and a rear pad portion interacts with the occipital area (see FIGS. 12G-12I).

The exterior/outer surface of the head pad can be constructed of a variety of materials including closed cell foam, open cell foam, etc, preferably one that insulates the therapy-providing fluid flowing through the channels from ambient air. The channels, attached to the exterior/outer surface through which the liquid flows may be constructed of vinyl, polyurethane, etc. The channels are formed by heat sealing the material or some other process. The channeled material may be covered with some other type of material (e.g. fabric, plush, etc.) or could be in direct contact with the wearer's tissue. The channels can be configured with rounded or square corners and any number of flow patterns could be employed. For example, as is shown in FIG. 12F, fluid can enter the channels on opposite lower ends of the fore pad portion at inlets 440, 441 and exit the channels on its opposite upper ends at outlets 450, 451. As illustrated, the fluid channel 460 has contiguous sidewalls 461 defining a single restricted flow path 462. The fluid channel 460 may include a first set of segments 464 forming a first portion 465 of the single restricted flow path and a second set of segments 466 forming a second portion 467 of the single restricted flow path. These sets of segments may be serially connected to each other to form the single restricted flow path 462. Further, the space between the sidewalls defining the single restricted flow path may be relatively thin, having a width, for example, that is less than one-third a width of the body pad measured in a direction transverse to the flow path and in a plane of the body pad at all points along the flow path, as is illustrated. As is shown in FIG. 12I, fluid can enter channels on the opposite upper ends of the rear pad portion and exit the channels on its opposite lower ends. Any flow pattern can be employed which provides the desired thermal distribution, flow and comfort.

Molded rigid or semi rigid plastic attachments or inserts 410 may be incorporated at various locations throughout the pad to provide contour to the channeled surface for improved contact, fit, and comfort. The pad may be adjustable through the inclusion of hook-and-loop fastening straps. In addition to adjusting for fit, the pad can also be adjusted for varying levels of compression. The pad could also incorporate an eye covering to block light (with or without channels). The device 400 could include pads which deliver thermal therapy to a single trigger point (e.g. forehead) or to any combinations of trigger points (e.g. forehead and occipital, forehead and TMJ, TMJ and occipital, etc.) The plastic inserts can be formed with a concave shape relative to the head, so as to apply slight pressure, thus increasing the effectiveness of thermal transfer. (These pressure inserts can also be used in any tissue-interacting device 400, and are not limited to head pads.)

FIG. 13A and FIG. 13B also show the tissue-interacting device 400 as a head pad. In FIG. 13A, the head pad is designed to fit over the forehead and temples, delivering therapy to specifically known trigger point areas for migraines. In FIG. 13B, the head pad is designed to fit the back of the head and occipital area. A head pad delivering therapy to both the front and back portions of the head is also possible.

FIGS. 14A-14E show the tissue-interacting device 400 as an eye pad. The eye pad is specifically designed to deliver thermal therapy to the periorbital area of the eye to provide relief to this area following eye surgery, sinus headaches, and/or to individuals with swelling/puffiness in this area, dry eye sufferers, for general relaxation, etc. The eye pad is comprised of two individual pad portions (i.e., a left pad portion and a right pad portion) designed to fit into and around the periorbital area. The individual pads may be permanently connected or connected via some other means which allow for complete separation and/or adjustment of the distance between the two pads (e.g. hook-and-loop fastener). The exterior/outer surface of the pad assembly may be constructed of a variety of materials including closed cell foam, open cell foam, etc. The channels through which the liquid flows may be constructed of vinyl, polyurethane, etc. The channels are formed by heat sealing the material or some other process. The channeled material may be covered with some other type of material (e.g. fabric, plush, etc.) or could be in direct contact with the wearer's tissue.

As is best seen in FIG. 14E, the channels can be configured with rounded or square corners and any number of flow patterns could be employed. In the illustrated embodiment, each eye pad portion has its own inlet and outlet for the therapy-providing fluid. This may assist in helping to maintain equal temperatures in each half. In order to achieve the desired fit into and around the contours of the periorbital area, the eye pads are shaped and contoured through the use of inserts between the exterior/outer surface and the channeled layer(s). This shape and contour can be achieved via a variety of materials including foam, silicone, liquid, etc.

The eye pad may be adjustable through the inclusion of hook-and-loop fastening straps which wrap around the head. In addition to adjusting for fit, the pad can also be adjusted for varying levels of compression. The pads may include holes in the center to permit vision or may be solid to block light and create an occlusive environment. Alternatively, if holes are present, optional inserts/coverings could be included which would allow the user to alternate between covered and uncovered eye openings. Additionally, the eye hole coverings could be coupled with a material such as foam which would enable the addition of moisture (pre-soaking foam in water) to create a moist environment for the eyes.

Variations could include pads which deliver thermal therapy to a single trigger point (e.g., forehead) or to any combinations of trigger points (e.g., forehead and occipital, forehead and TMJ, TMJ and occipital, etc.)

Referring now to FIGS. 15A-15C, another embodiment of the tissue-interacting device 400 is shown, this device being a body pad shaped/sized to enable thermal therapy anywhere on the body. The exterior/outer surface of the pad assembly may be constructed of a variety of materials including closed cell foam, open cell foam, etc. The channels through which the liquid flows may be constructed of vinyl, polyurethane, etc. The channels are formed by heat sealing the material or some other process. The channeled material may be covered with some other type of material (e.g. fabric, plush, etc.) or could be in direct contact with the wearer's tissue. Straps of various forms may be included to enable securing the pad to the body part being treated. As is best seen in FIG. 15C, in the illustrated embodiment, the therapy-providing fluid has one entrance and one exit and these are positioned adjacent to each other. Also, the channel paths cover, substantially and evenly, most of the rectangular surface area of the pad. More entrances/exits, different positionings thereof, are certainly possible and contemplated. Also, the fluid channels could be patterned so that certain areas are more densely occupied than others to target these particular areas.

FIG. 16 shows the tissue-interacting device 400 as a knee pad designed to fit over and provide therapy to the knee area. FIG. 17 shows the tissue-interacting device 400 as an elbow pad. In FIG. 18, the device 400 is designed to fit over and provide therapy to the ankle/foot area. And FIG. 19 shows a tissue-interacting device 400 designed to fit over and provide therapy to the shoulder and neck area.

In addition to the embodiments described and illustrated above, other tissue-interacting devices 400 are possible and contemplated. For example, the tissue-interacting device 400 could be designed without channels and instead could include fluid pockets. The fluid pockets would be formed in the tissue-interacting device, could contain a fluid, and could be sealed. Such a fluid may be heated or cooled by external thermal activity (e.g., heating the tissue-interacting device 400 in a container of hot fluid, heating the tissue-interacting device 400 in a microwave oven, or the like, cooling the tissue-interacting device 400 in a refrigerator or freezer or a container of cooled fluid, etc.). Alternatively, the tissue-interacting device may be designed as a disposable and/or one-use-type device that contains chemical components in the pockets that react thermally upon demand. For example, a "self-cooling" design may include a pocket with a portion of ammonium nitrate and second portion of water. Such a design could provide instant but temporary cooling when the two portions of chemicals are allowed to mix and interact with one another. Similarly, a "self-heating" pocket could be included making use of thermally reactive chemicals. In certain circumstances, replacement or recharge of the chemicals may allow such a device to be re-used multiple times.

One may now appreciate that the thermal therapy system 100 and/or the tissue-interacting device 400 can target significant areas whereby thermal therapy is efficiently and effectively delivered. Although this system 100 and/or the devices 200/300/400 have been shown and described with respect to a certain embodiment or embodiments, it is obvious that equivalent alterations and modifications will occur to others skilled in the art upon the reading and understanding of this specification and the annexed drawings. In regard to the various functions performed by the above described elements (e.g., components, assemblies, systems, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function. In addition, while a particular feature may have been described above with respect to only one or more of several illustrated embodiments, such a feature may be combined with one or more other features of the other embodiments, as may be desired and advantageous for any given or particular application.

The invention claimed is:

1. A thermal therapy system comprising:
 a device for interacting with tissue to provide thermal therapy to a structure of a therapy-receiving person's body;
 a fluid-manipulating device which heats/cools therapy-providing fluid including a pump for motivating the circulation of the therapy-providing fluid through the system and a heat exchanger for heating/cooling the therapy-providing fluid;

tubing, and associated fittings, between the tissue-interacting device and the fluid-manipulating device; and an electrical control for controlling the temperature of the therapy-providing fluid, wherein the heat exchanger comprises a heat sink, a channel in a block through which the therapy-providing fluid flows, and one or more thermoelectric devices placed in thermal contact with the sink and the block, wherein the heat exchanger is switchable between a cold mode and a heat mode by changing a polarity of the one or more thermoelectric devices, wherein the electrical control is configured to automatically prevent instant switching of the polarity of the one or more thermoelectric devices, to protect the one or more thermoelectric devices from thermal shock and damage, and wherein in response to a command to switch polarity, the electrical control is configured to turn power to the one or more thermoelectric devices off.

2. A thermal therapy system as set forth in claim 1, wherein at least some of the fittings comprise quick-disconnect fittings.

3. A thermal therapy system as set forth in claim 1, wherein the fluid-manipulating device comprises a fan which interacts with the heat exchanger heat sink.

4. A thermal therapy system as set forth in claim 1, wherein the device for interacting with tissue is a head pad.

5. A thermal therapy system as set forth in claim 4, wherein the head pad is designed to concentrate therapy in one or more trigger point areas for migraines.

6. A thermal therapy system as set forth in claim 5, wherein the one or more trigger point areas include at least one of the forehead area, the occipital area, or the TMJ areas.

7. A thermal therapy system as set forth in claim 6, wherein the head pad comprises a fore pad portion which concentrates on the forehead area and the TMJ areas.

8. A thermal therapy system as set forth in claim 4, wherein the head pad comprise a rear pad portion which concentrates on the occipital area.

9. A thermal therapy system as set forth in claim 1, wherein the tissue-interacting device is an eyepad.

10. A thermal therapy system as set forth in claim 1, wherein the tissue-interacting device comprises a rectangular pad.

11. A thermal therapy system as set forth in claim 1, wherein the tissue-interacting device is a knee pad, an elbow pad, an ankle/foot pad, or a neck/shoulder pad.

12. A thermal therapy system as set forth in claim 1, wherein the electrical control is configured to control a flow rate of the pump to achieve a desired temperature of the therapy-providing fluid.

13. A thermal therapy system as set forth in claim 1, wherein the tubing is radially enclosed in a layer of material for insulating the tubing.

14. A thermal therapy system as set forth in claim 1, further comprising spacers disposed between the thermoelectric devices for spacing the sink from the block and thereby providing insulation therebetween.

15. A thermal therapy system as set forth in claim 1, further comprising a reservoir, the reservoir and pump encased in a housing of the fluid manipulating device, the fluid manipulating device further comprising a fill port fluidly connected to the reservoir.

16. The thermal therapy system of claim 1, wherein in response to the command to switch polarity, the electrical control is configured to turn power to the one or more thermoelectric devices off for a predetermined length of time before power is restored and the polarity is switched.

17. The thermal therapy system of claim 16, wherein the predetermined length of time is sufficient to prevent thermal shock to the one or more thermoelectric devices.

18. The thermal therapy system of claim 17, wherein the predetermined length of time is about five minutes.

\* \* \* \* \*